(12) United States Patent
Ek et al.

(10) Patent No.: US 9,533,140 B2
(45) Date of Patent: *Jan. 3, 2017

(54) MICROELECTRODE AND MULTIPLE MICROELECTRODES

(71) Applicants: Fredrik Ek, Lund (SE); Nils Danielsen, Genarp (SE); Jenny Eriksson Linsmeier, Höllviken (SE); Per Petersson, Lund (SE); Jens Schouenborg, Lund (SE)

(72) Inventors: Fredrik Ek, Lund (SE); Nils Danielsen, Genarp (SE); Jenny Eriksson Linsmeier, Höllviken (SE); Per Petersson, Lund (SE); Jens Schouenborg, Lund (SE)

(73) Assignee: NEURONANO AB (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/329,339

(22) Filed: Jul. 11, 2014

(65) Prior Publication Data

US 2014/0323948 A1    Oct. 30, 2014

Related U.S. Application Data

(63) Continuation of application No. 13/376,910, filed as application No. PCT/SE2010/000152 on Jun. 3, 2010, now Pat. No. 8,954,142.

(30) Foreign Application Priority Data

Jun. 9, 2009    (SE) ...................................... 0900789

(51) Int. Cl.
*A61L 31/16* (2006.01)
*A61L 31/14* (2006.01)
(Continued)

(52) U.S. Cl.
CPC ............. *A61N 1/05* (2013.01); *A61B 5/04001* (2013.01); *A61L 31/148* (2013.01); *A61L 31/16* (2013.01);
(Continued)

(58) Field of Classification Search
CPC .................... A61L 2300/604; A61L 2300/606; A61L 31/148; A61L 31/16; A61N 1/0412; A61N 1/0476; A61N 1/05; A61N 1/0502; A61N 1/0504; A61N 1/0531; A61N 1/0536; A61N 1/0551; A61N 1/306; A61N 1/37205
See application file for complete search history.

(56) References Cited

U.S. PATENT DOCUMENTS

| 3,724,467 A | 4/1973 | Avery et al. .................. 128/418 |
| 3,822,708 A | 7/1974 | Zilber ........................... 128/419 |

(Continued)

FOREIGN PATENT DOCUMENTS

| EP | 669128 B1 | 8/1995 |
| WO | WO 98/012243 A1 | 3/1998 |

(Continued)

OTHER PUBLICATIONS

Supplementary European Search Report dated Oct. 30, 2012, issued in corresponding European Application No. 10 786 433.2.
(Continued)

*Primary Examiner* — Quynh-Nhu H Vu
(74) *Attorney, Agent, or Firm* — Ostrolenk Faber LLP

(57) ABSTRACT

A medical microelectrode includes an elongate electrode body including a tip section, a main body section and, optionally, a coupling section. The tip section, the main body section and, optionally, the coupling section are embedded in a first electrode matrix element, which is substantially rigid, biocompatible and soluble or biodegradable in a body
(Continued)

fluid. Additionally the microelectrode includes a dissolution retarding layer on the first electrode matrix element and/or a second electrode matrix element disposed between the first electrode matrix element and the electrode. Upon dissolution or biodegradation of the first electrode matrix element a drug comprised by the first electrode matrix element or the second electrode matrix element is released into the tissue. Also disclosed are bundles and arrays of the electrodes and their use.

8 Claims, 17 Drawing Sheets

(51) Int. Cl.

| | | |
|---|---|---|
| A61N 1/00 | (2006.01) | |
| A61N 1/05 | (2006.01) | |
| A61B 5/04 | (2006.01) | |
| A61N 1/04 | (2006.01) | |
| A61N 1/30 | (2006.01) | |
| A61N 1/32 | (2006.01) | |
| A61N 1/372 | (2006.01) | |
| A61B 5/00 | (2006.01) | |

(52) U.S. Cl.
CPC ........... *A61N 1/0531* (2013.01); *A61N 1/0536* (2013.01); *A61N 1/0551* (2013.01); *A61B 5/4094* (2013.01); *A61L 2300/604* (2013.01); *A61N 1/0412* (2013.01); *A61N 1/0476* (2013.01); *A61N 1/306* (2013.01); *A61N 1/325* (2013.01); *A61N 1/327* (2013.01); *A61N 1/37205* (2013.01)

(56) References Cited

U.S. PATENT DOCUMENTS

| | | | |
|---|---|---|---|
| 3,995,560 A | 12/1976 | Mackintosh | 104/1 |
| 4,379,462 A | 4/1983 | Borkan et al. | 128/786 |
| 4,573,481 A | 3/1986 | Bullara | 128/784 |
| 4,852,573 A | 8/1989 | Kennedy | 128/642 |
| 4,920,979 A | 5/1990 | Bullara | 128/784 |
| 5,031,621 A | 7/1991 | Grandjean et al. | 128/642 |
| 5,202,120 A | 4/1993 | Silver et al. | 424/91 |
| 5,215,008 A | 6/1993 | Kartovaara et al. | 100/47 |
| 5,380,299 A | 1/1995 | Fearnot et al. | 604/265 |
| 5,417,719 A | 5/1995 | Hull et al. | 607/46 |
| 5,501,703 A | 3/1996 | Holsheimer et al. | 407/46 |
| 5,741,319 A | 4/1998 | Woloszko et al. | 607/118 |
| 5,820,589 A | 10/1998 | Torgerson et al. | 604/93 |
| 5,957,958 A | 9/1999 | Schulman et al. | 607/56 |
| 6,027,721 A | 2/2000 | Hammang et al. | 424/93.2 |
| 6,032,062 A | 2/2000 | Nisch | 600/373 |
| 6,042,875 A | 3/2000 | Ding et al. | 427/2.24 |
| 6,253,110 B1 | 6/2001 | Brabec et al. | 607/116 |
| 6,316,018 B1 | 11/2001 | Ding et al. | 424/423 |
| 6,375,655 B1 | 4/2002 | Zdeblick et al. | 606/51 |
| 6,421,566 B1 | 7/2002 | Holsheimer | 607/46 |
| 6,436,708 B1 | 8/2002 | Leone et al. | 435/458 |
| 6,471,688 B1 | 10/2002 | Harper et al. | 604/892.1 |
| 6,632,217 B2 | 10/2003 | Harper et al. | 604/892.1 |
| 6,993,392 B2 | 1/2006 | Nicolelis et al. | 607/45 |
| 7,041,492 B2 | 5/2006 | Oka et al. | 435/285.2 |
| 7,066,904 B2 | 6/2006 | Rosenthal et al. | 604/103.08 |
| 7,099,718 B1 | 8/2006 | Thacker et al. | 607/117 |
| 7,146,221 B2 | 12/2006 | Krulevitch et al. | 607/36 |
| 7,229,477 B2 | 6/2007 | Biscup | 623/17.11 |
| 7,351,239 B2 | 4/2008 | Gill | 604/890.1 |
| 7,471,689 B1 | 12/2008 | Tripathi et al. | 370/395.5 |
| 8,010,208 B2 * | 8/2011 | Nimer | A61N 1/05 607/115 |
| 2005/0187146 A1 | 8/2005 | Helmus et al. | 514/8 |
| 2007/0073130 A1 | 3/2007 | Finch et al. | 600/372 |
| 2007/0088417 A1 | 4/2007 | Schouenborg | 607/116 |
| 2007/0197892 A1 | 8/2007 | Shen et al. | 600/378 |
| 2007/0198063 A1 | 8/2007 | Hunter et al. | 607/3 |
| 2008/0177363 A1 * | 7/2008 | Schouenborg | A61N 1/0529 607/116 |
| 2008/0234790 A1 | 9/2008 | Bayer et al. | 607/116 |
| 2009/0043369 A1 * | 2/2009 | Radeloff | A61N 1/0541 607/137 |
| 2011/0009728 A1 * | 1/2011 | Schouenborg | A61N 1/0551 600/373 |

FOREIGN PATENT DOCUMENTS

| | | |
|---|---|---|
| WO | WO 00/01300 A1 | 1/2000 |
| WO | WO 2005/067896 A1 | 7/2005 |
| WO | WO 2005/082430 A1 | 9/2005 |
| WO | WO 2005/105053 A1 | 11/2005 |
| WO | WO 2007/040442 A1 | 4/2007 |
| WO | WO 2007/134315 A1 | 11/2007 |
| WO | WO 2008/038197 A1 | 4/2008 |
| WO | WO 2008/091197 A1 | 7/2008 |
| WO | WO 2008/150974 A1 | 12/2008 |
| WO | WO 2009/052425 A1 | 4/2009 |
| WO | WO 2009/075625 A1 | 6/2009 |

OTHER PUBLICATIONS

International Search Report dated Sep. 16, 2010, issued in corresponding International Application No. PCT/SE2010/000152.
Abidian et al., "Multifunctional nanobiomaterials for neural interfaces," Advanced Functional Materials, Feb. 2009, vol. 19, nr. 4, pp. 573-585; p. 573, col. 1, p. 582, col. 2.7, figure 1.
Abidian et al., "Conducting-polymer nanotubes for controlled drug release," Advanced Materials, Feb. 2006, vol. 18, nr. 4, pp. 405-409; p. 405, col. 2, p. 407, col. 1.
Mercanzini et al., "The effect of biodegradable drug release coatings on the electrical characteristics of neural electrodes," 14th International Conference on Solid-State Sensors, Actuators and Microsystems, US 2007, pp. 1377-1380.
Mercanzini et al., "Controlled release drug coatings on flexible neural probes," Annual International Conference of the IEEE Engineering in Medicine and Biology Society, US 2007, vol. 2007, pp. 6613-6616; p. 6612, part 1, figure 2.
DiPaolo et al., "Nanofiber scaffolding for improved neural electrode biocompatibility," Proceedings of the IEEE 29th Annual Northeast Bioengineering Conference, US 2003, p. 21-22.
Kim, Seon Jeonge, et al., Electric Stimuli Responses to Poly(vinyl alcohol)/Chitosan Interpenetrating Polymer Network Hydrogel in NaCl Solutions, Journal of Applied Polymer Sciences, vol. 86, pp. 2285-2289 (2002).
Polikov, et al., "Response of brain tissue to chronically implanted neural electrodes," Journal of Neuroscience Methods 148 (2005) 1-18.
Sofronniew, Michael V., "Reactive Astrocytes in Neural Repair and Protection," The Neuroscientist, ISSN 1073-8584, pp. 400-407.
Storek, et al., "Reconstitution of the immune system after hematopoietic stem cell transplantation in humans," Semin Immunopathol (2008) 30:425 425-437.
Norton, William T., "Cell Reactions Following Acute Brain Injury: A Review," Neurochemical Research, vol. 24, No. 2, 1999, pp. 213-218.

* cited by examiner

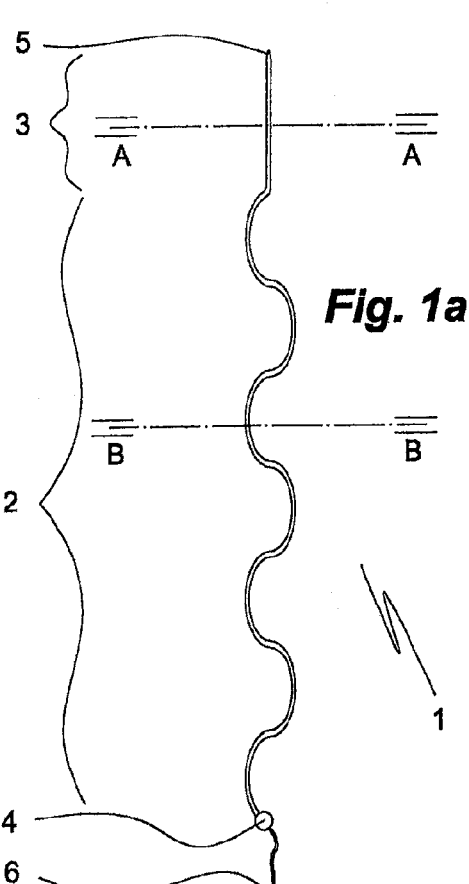
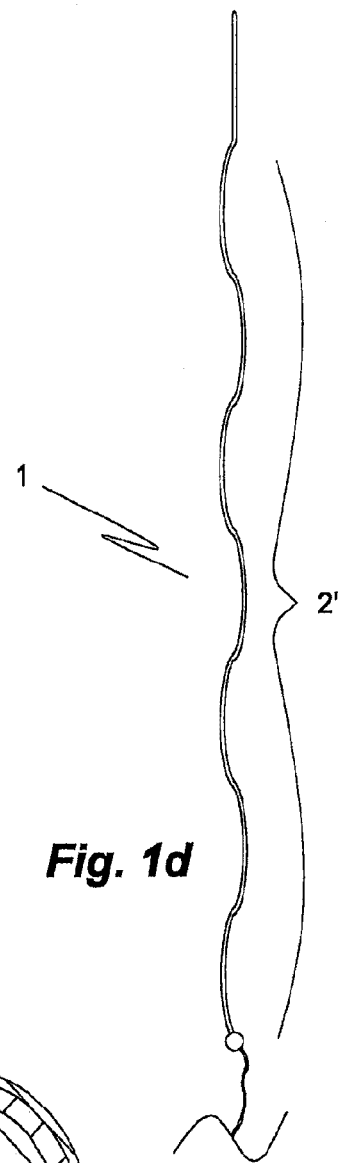
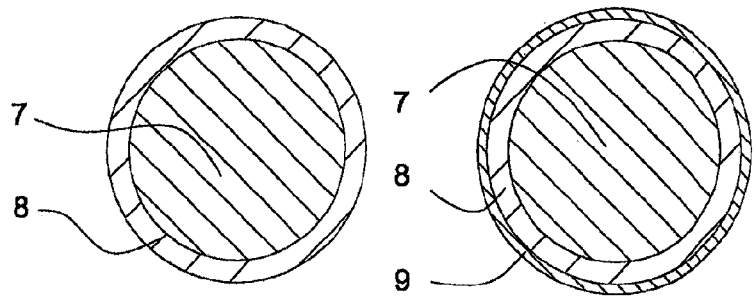
Fig. 1a
Fig. 1d
Fig. 1b
Fig. 1c

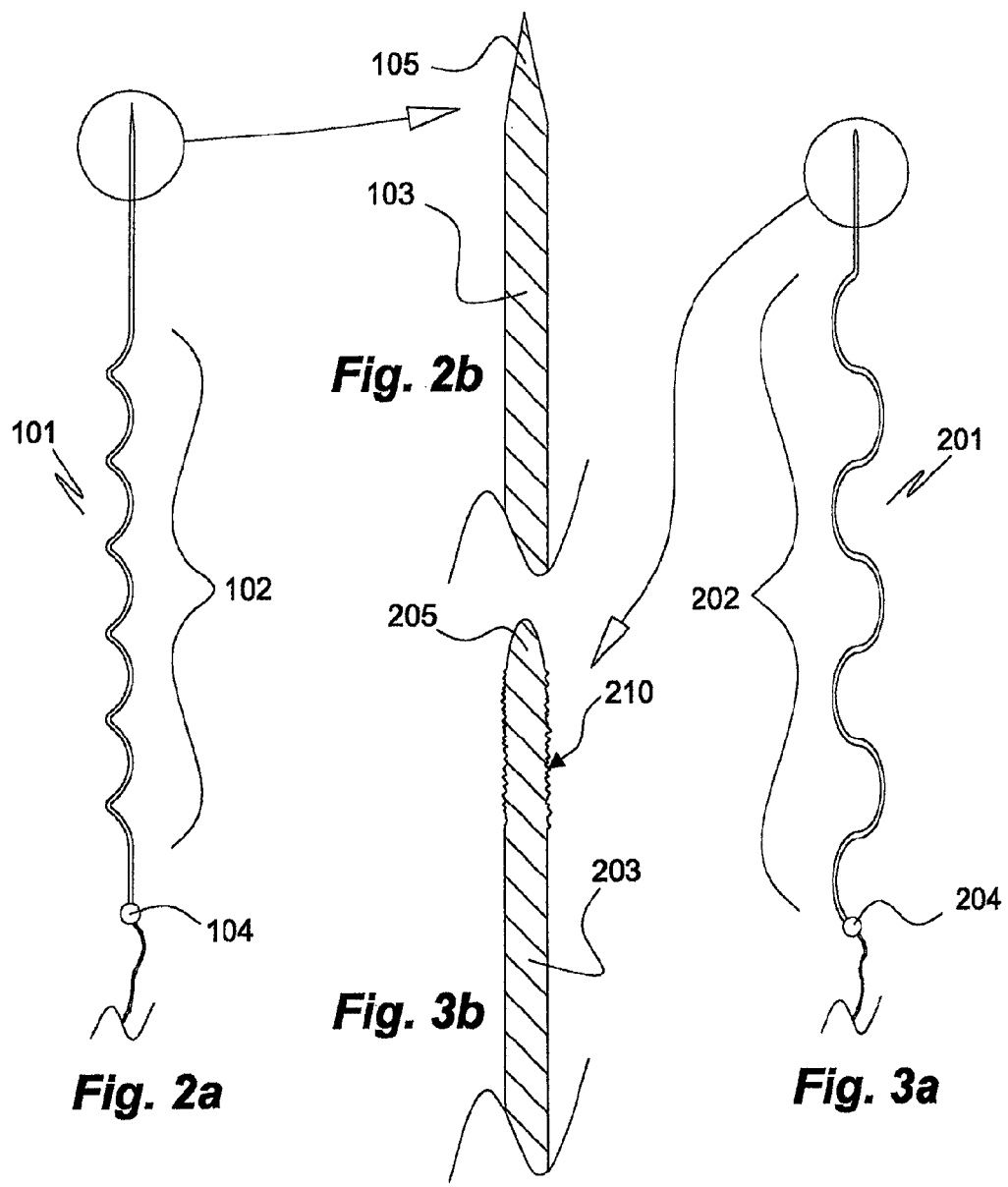

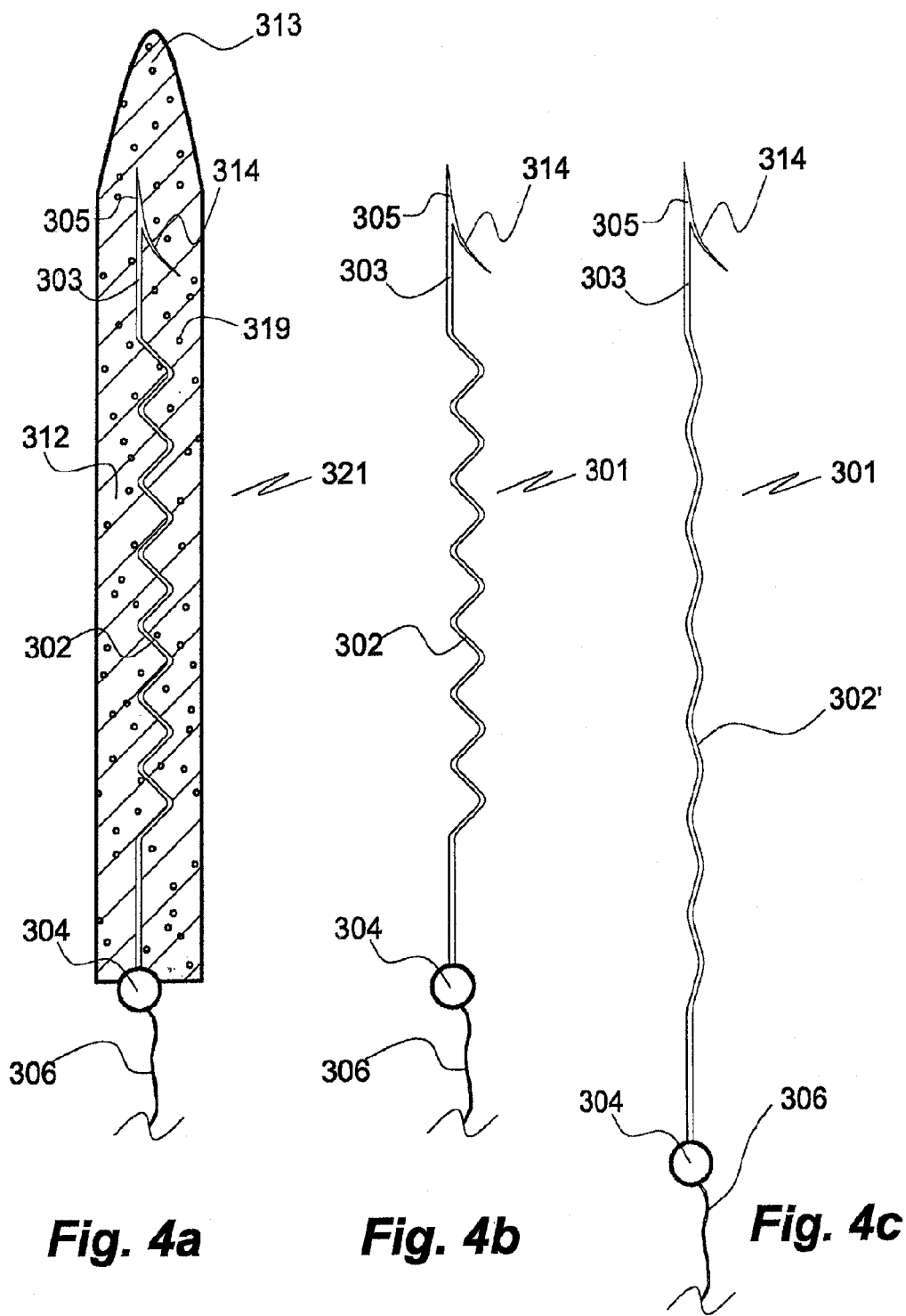

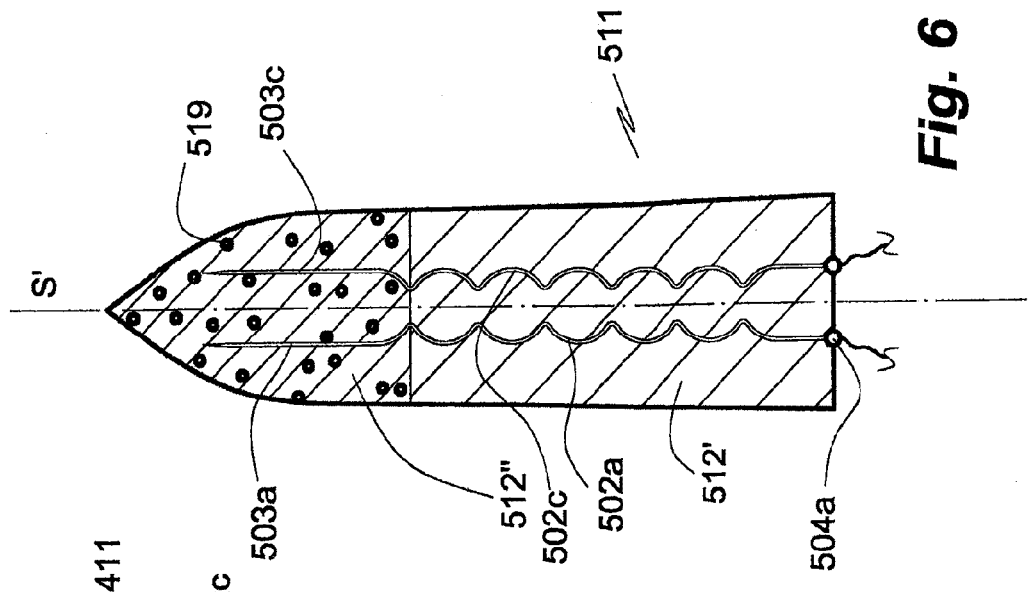
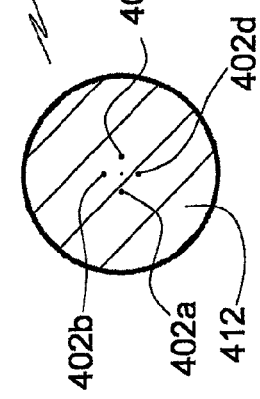
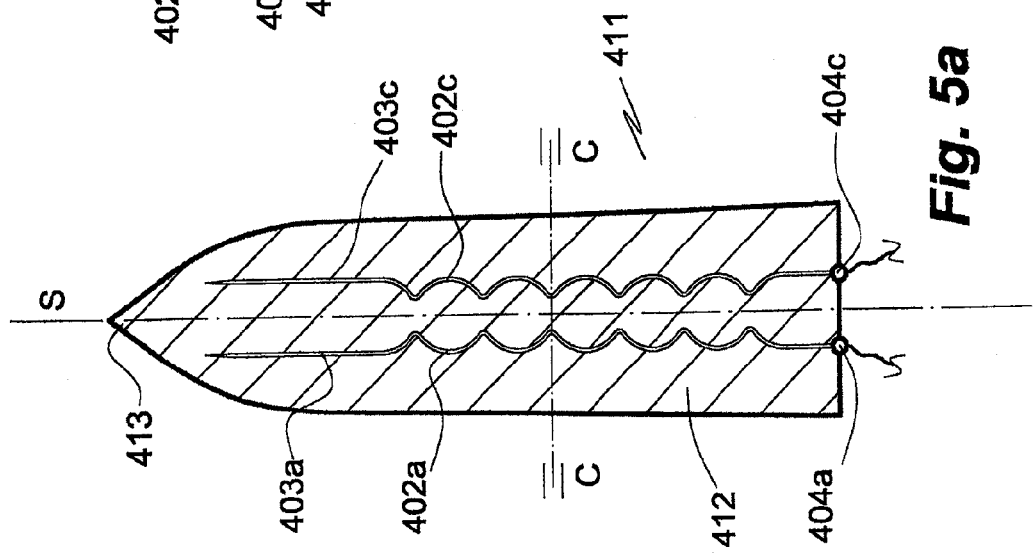

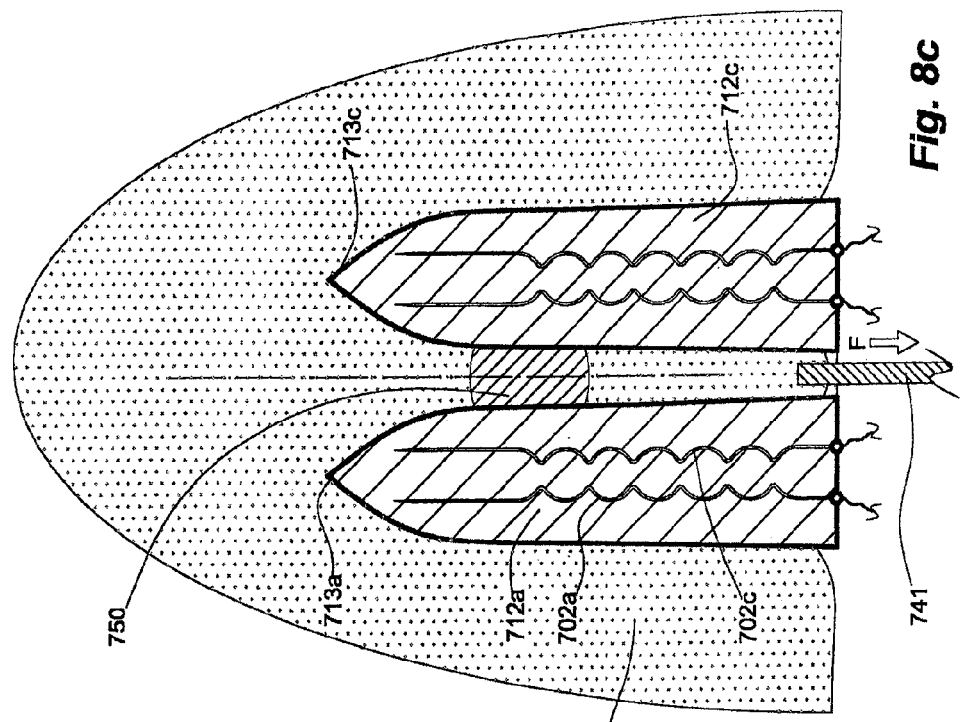
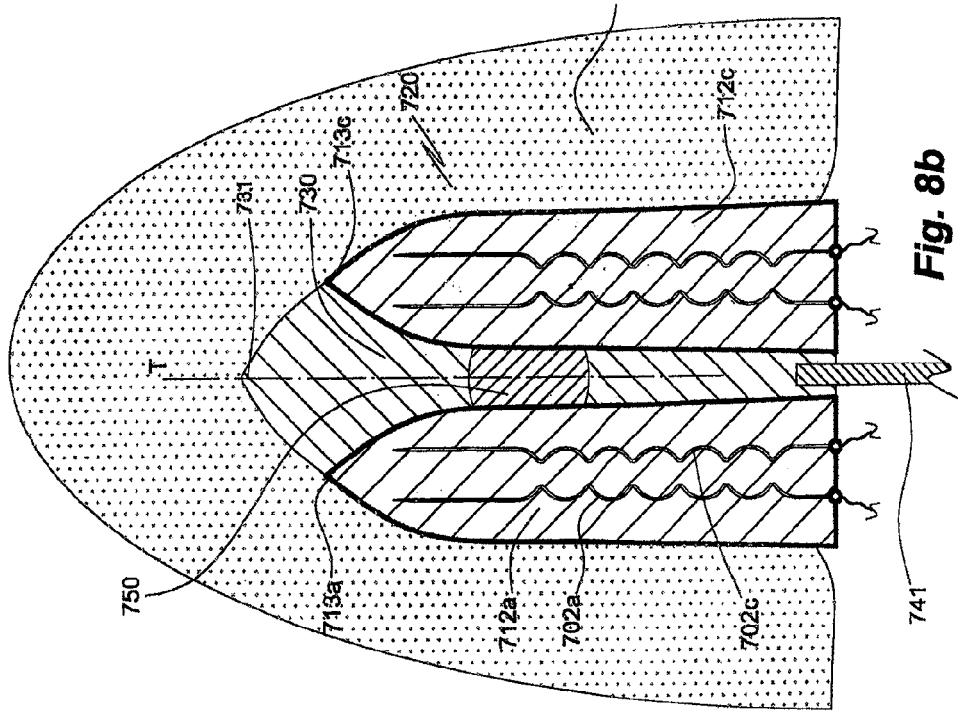

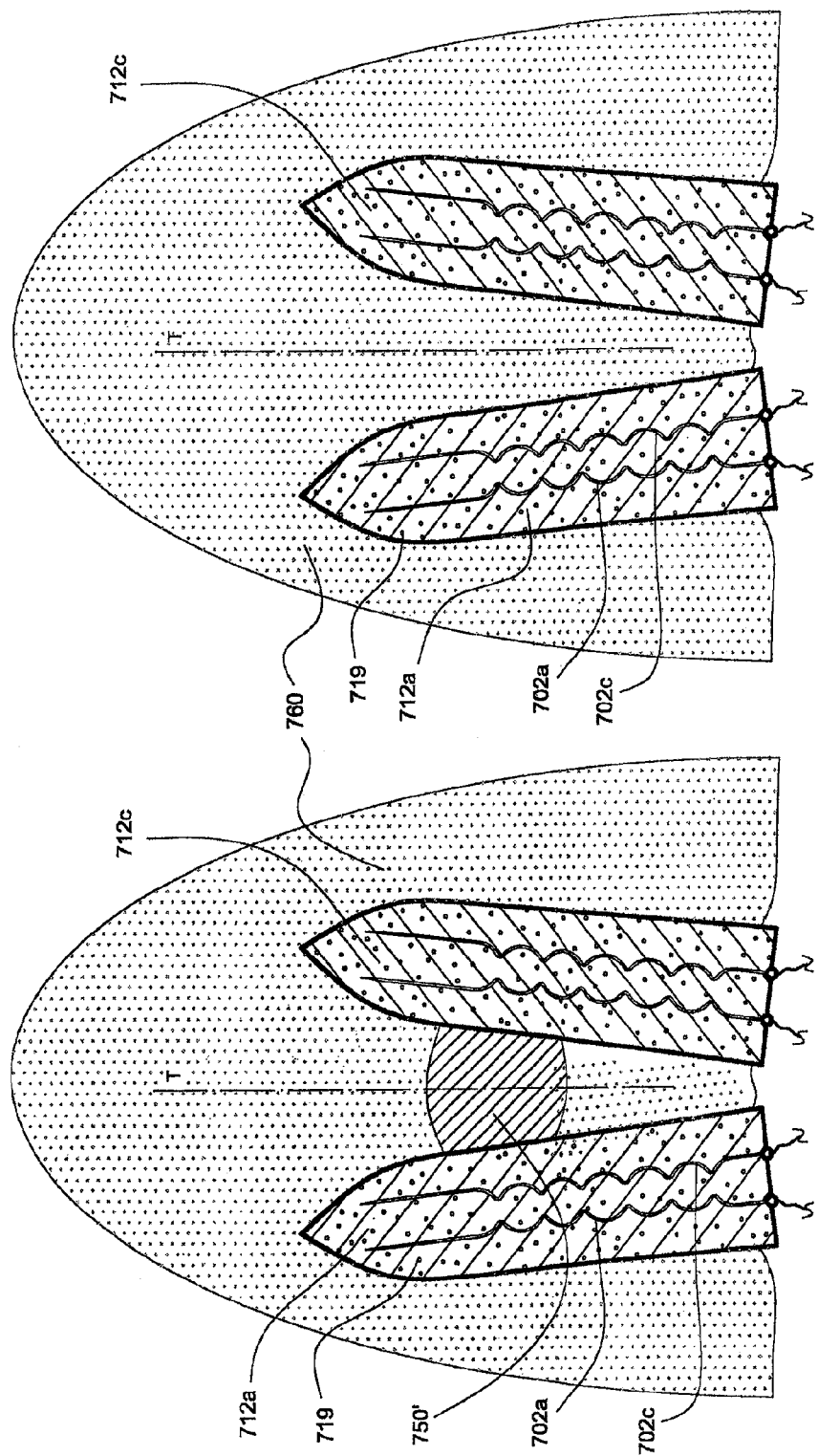

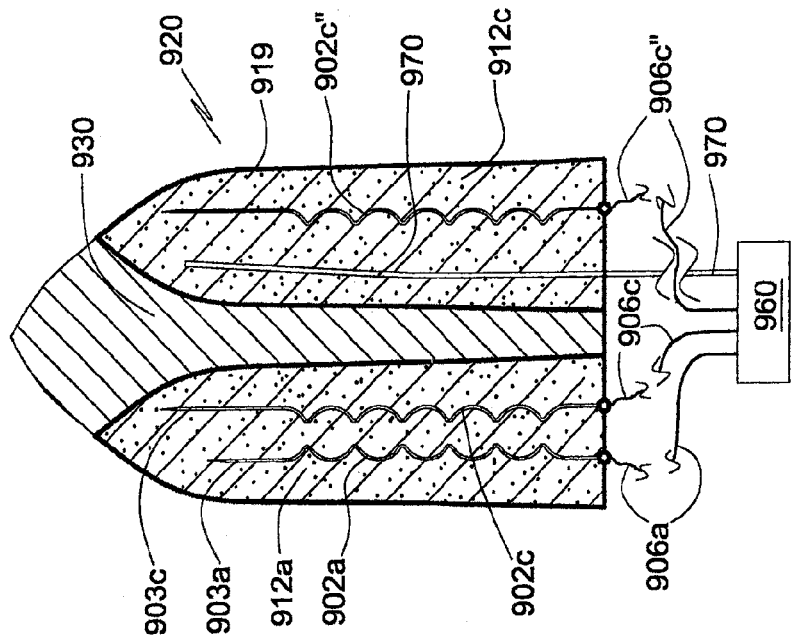
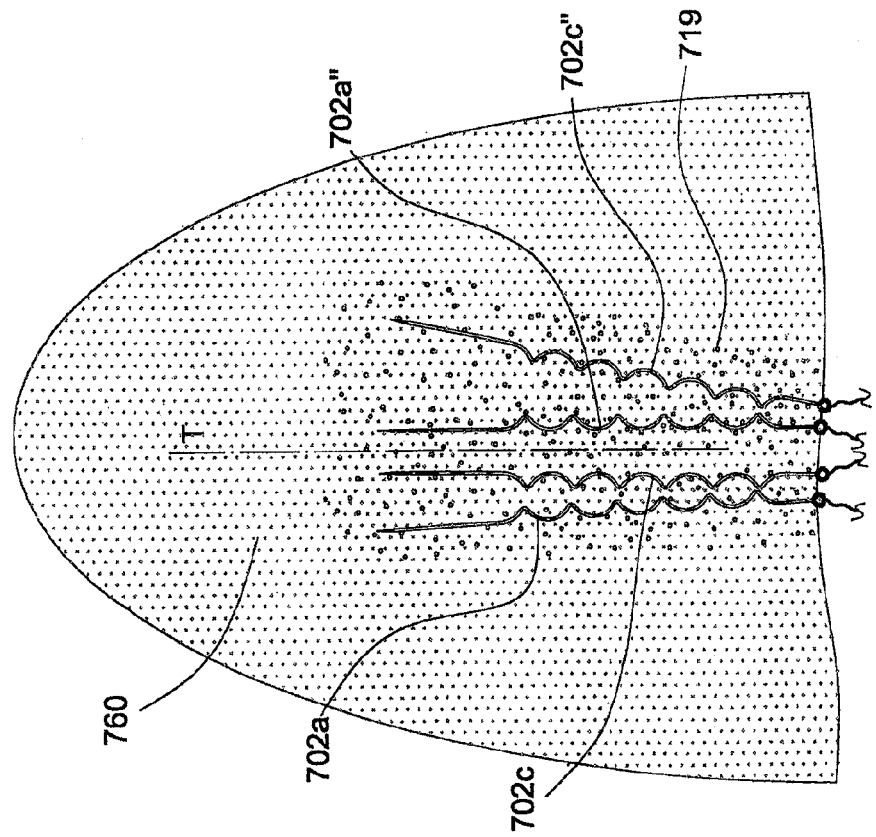
Fig. 9
Fig. 8f

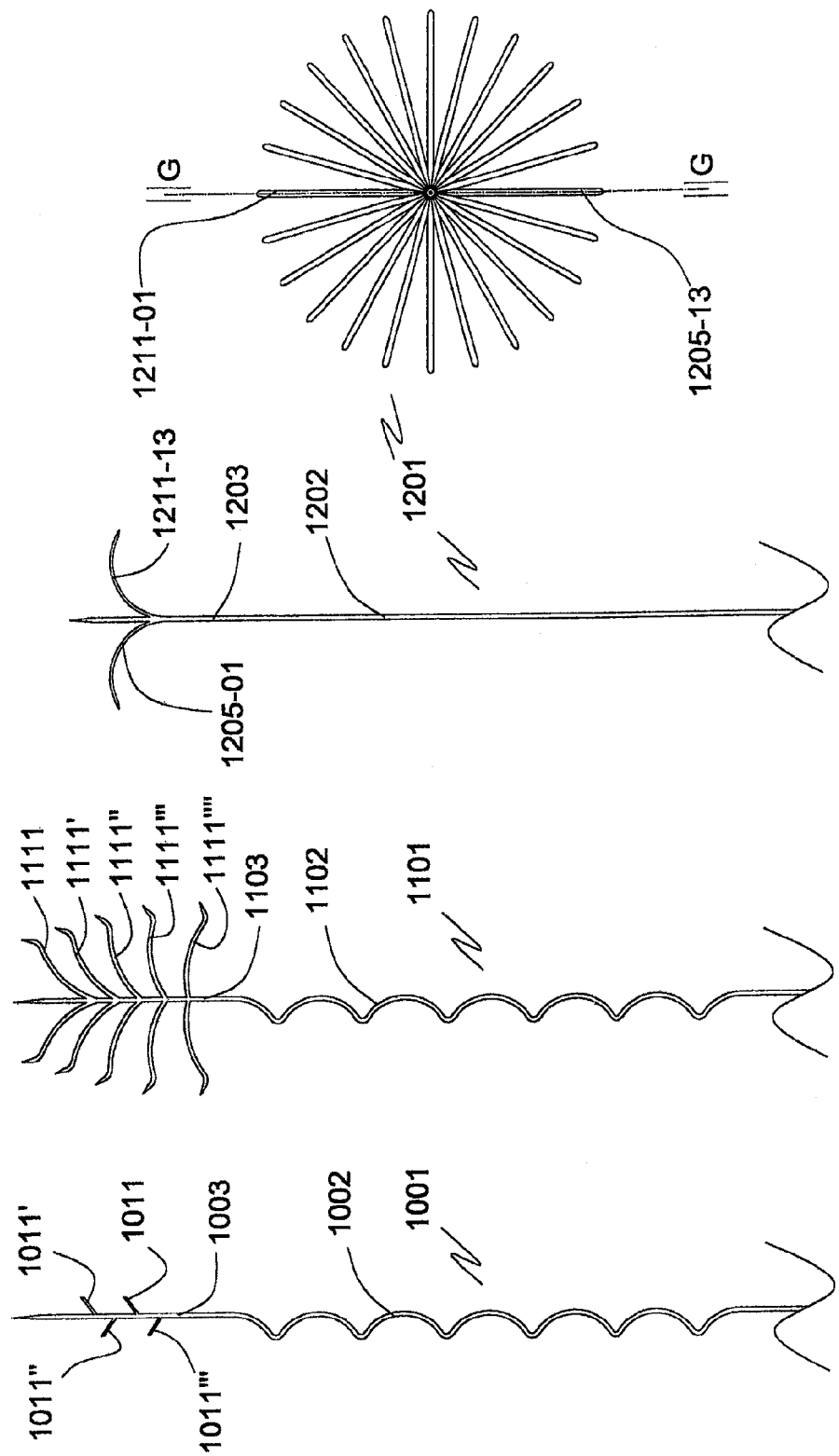

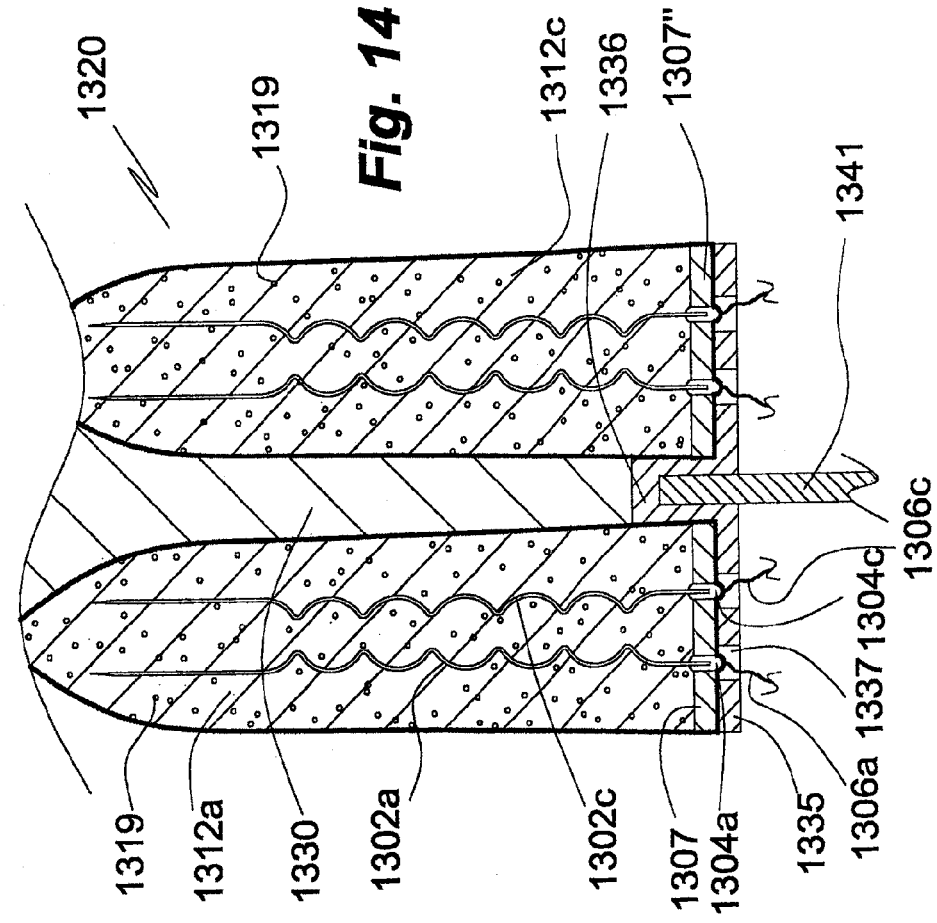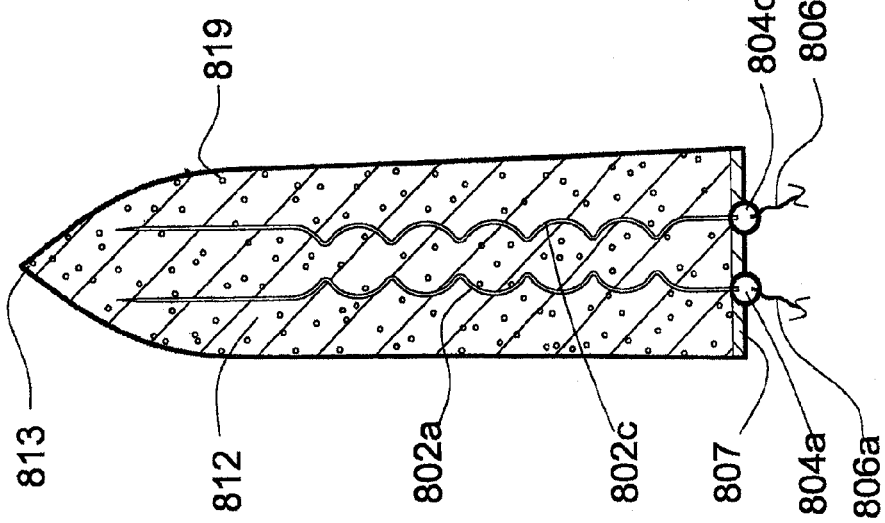

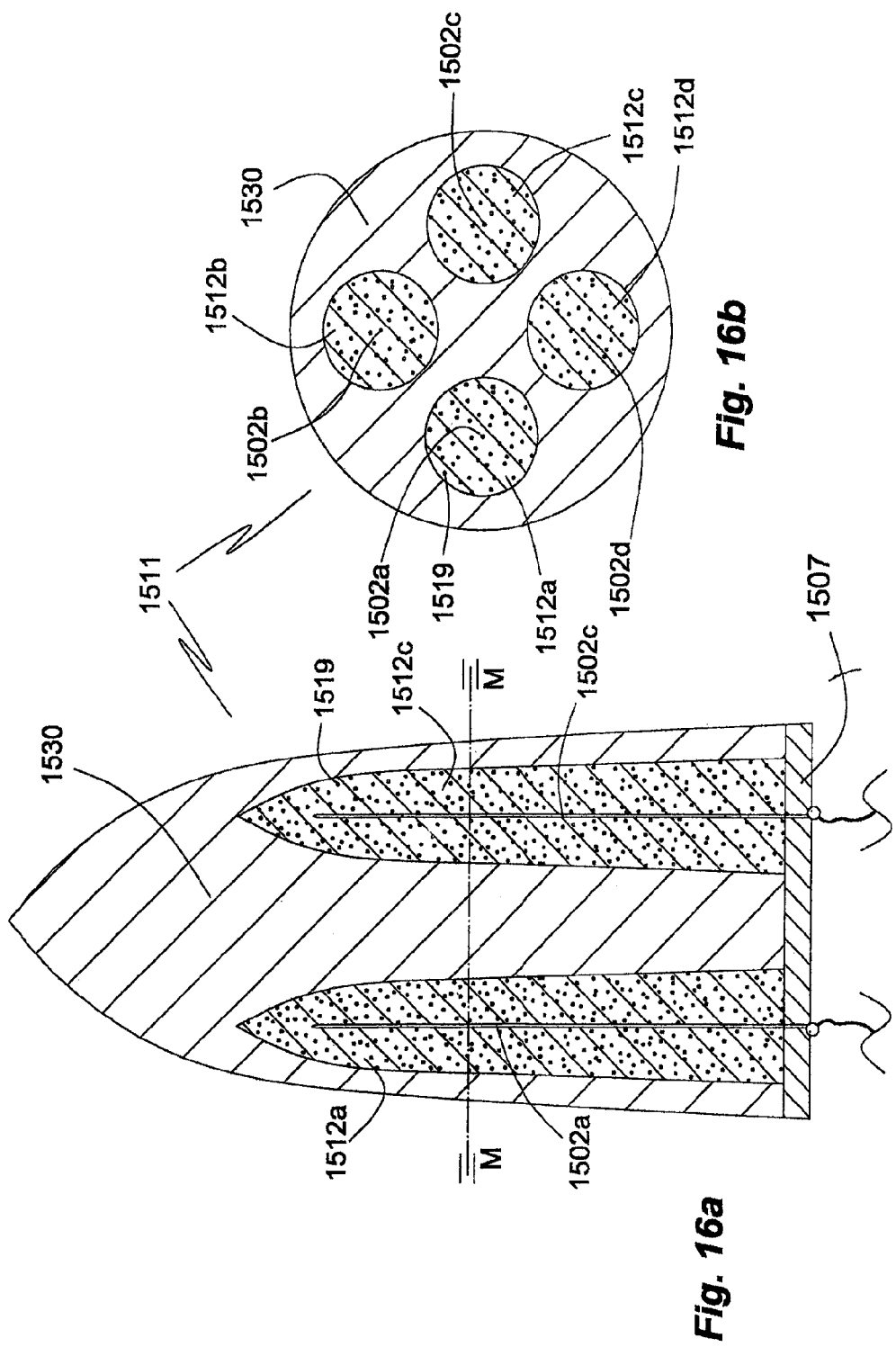

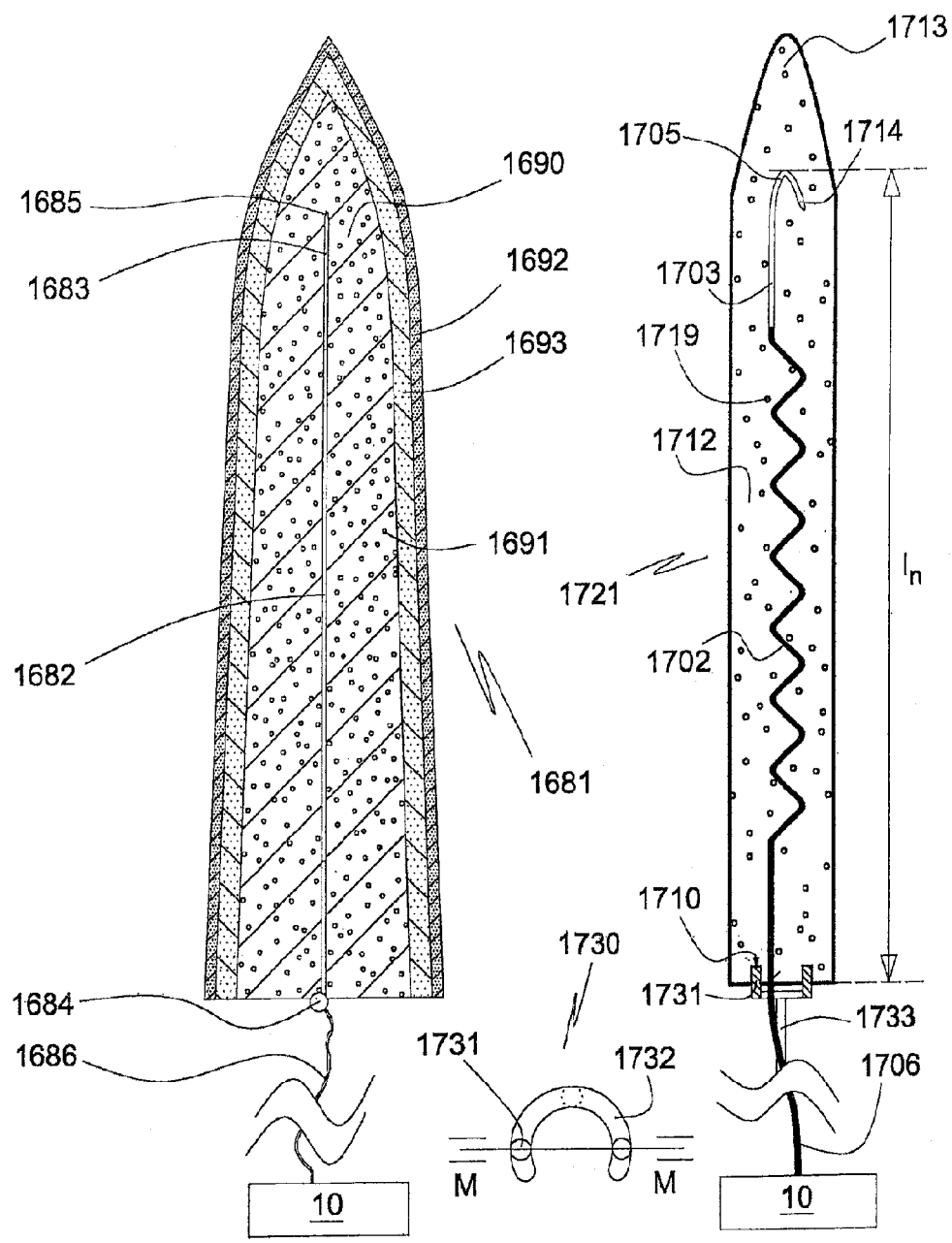
*Fig. 18*  *Fig. 19a*  *Fig. 19*

MICROELECTRODE AND MULTIPLE MICROELECTRODES

CROSS-REFERENCE TO RELATED APPLICATIONS

The present application is a continuation application under 37 C.F.R. §1.53(b) and 35 U.S.C. §121 of prior U.S. patent application Ser. No. 13/376,910, filed Jan. 31, 2012, by Fredrik Ek et al., entitled MICROELECTRODE AND MULTIPLE MICROELECTRODES, which is a 35 U.S.C. §371 National Phase U.S. application based on PCT/SE2010/000152, filed Jun. 3, 2010, which claims benefit of Swedish Application No. 0900789-9, filed Jun. 9, 2009. The PCT International Application was published in the English language. The contents of each of the patent applications above-listed are incorporated in full by reference herein.

FIELD OF THE INVENTION

The invention relates to a medical microelectrode and to multiple medical microelectrodes. In particular, the invention relates to a medical microelectrode, to a bundle of microelectrodes, and to an array of microelectrodes and/or microelectrode bundles. The microelectrode, microelectrode bundle and array of microelectrodes or microelectrode bundles of the invention are intended for insertion into soft tissue such as the brain, the spinal cord, endocrine organs, muscles, and connective tissue.

BACKGROUND OF THE INVENTION

Microelectrodes that can be implanted for a long time into the central nervous system (CNS) have a wide field of application. In this invention, the term "electrode" refers to a microelectrode. In principle, all brain nuclei can be recorded from or stimulated by such electrodes and their functions monitored. Of particular importance is the use of a multichannel design in brain nuclei stimulation. In such a design groups of electrodes or even individual electrodes can be addressed separately. This allows the user to select those electrodes whose stimulation produces a therapeutic effect that is improved in comparison with unselective stimulation. Stimulation of the brain or spinal cord can be of particular value in situations when brain nuclei are degenerated or injured. In certain situations it would also be useful to be able to combine controlled electrical stimulation and local gene transfer. A multichannel design may also allow the user to effectively measure the effects on multiple neurones and other cells following systemic or local drug administration or gene transfer. Of particular interest is an ability to simultaneously measure the effects of multiple drug candidates on neuronal function. Monitoring brain activity through implanted electrodes can also be useful if used to control drug delivery either locally or systemically or other therapeutic methods such as electrical stimulation of brain nuclei. Multichannel electrodes may also be used to lesion specific and circumscribed sites in tissue after abnormal impulse activity has been detected by recordings from the electrodes or by imaging such as fMRI or PET.

To record and stimulate brain structures various forms of implantable electrodes have been developed (U.S. Pat. Nos. 6,253,110 B1, 5,957,958, 4,573,481, 7,146,221 B2, 5,741,319, 4,920,979, 5,215,008, 5,031,621, 6,993,392 B2, 6,032,062, 4,852,573, 3,995,560, 7,041,492, 6,421,566 B1, 4,379,462, 5,417,719, 3,822,708, 5,501,703, 7,099,718 B1, 3,724,467; US 2007/0197892 A1). However, little attention has been paid to the injuries and complications caused by the implantation procedure. Not only can these consequences lead to an impaired function of the implant, they may also harm the individual in which the electrodes are implanted. The function of the implanted electrodes and also of the tissue, in which the implant is introduced, may be impaired due to either 1) acute injury of the tissue including bleeding and infarction of the tissue, 2) infection, 3) tissue reactions including inflammation and glial activation caused by the implantation procedure, 4) long lasting tissue reaction including glial activation and scar formation isolating the implant, and/or 5) movements between electrode and tissue. These consequences usually occur during different time intervals during and after the implantation:

1) When implanting microelectrodes in central nervous tissue there is, besides the general risk of open surgery, local risks such as bleedings and also infarctions of the tissue. Electrodes may punctuate blood vessels during implantation. This may cause bleeding and vasoconstriction. A strong inflammatory response to blood cells and proteins that leaked into the neural tissue can be thus triggered and might affect the tissue over extended periods of time. This may in turn induce cell death in the area supplied by the affected vessel. As a consequence the function of the electrode implant can be impaired.

2) General surgery and particular implantation of artificial devices also increase the risk of infections. The surgical area may be infected at the time of surgery or within the early recovery phase after surgery. The presence of a foreign body material (the implant itself) can also function as a locus minoris for establishing an infection in the tissue surrounding the electrodes. Tissue infections around implants are in general more difficult to treat with antibiotics than other tissue infections. Infections close to the implanted electrodes may besides impairing the function of the tissue also jeopardize the function of the implanted electrodes and may in extreme cases require removal of the device in order to cure the infection.

In addition to the general protection of systematically administered antibiotics it would be advantageous to be able to treat infections close to the implanted electrodes locally.

3) Implantation of electrodes into central nervous tissue will due to the inflicted injury always cause an acute inflammation (Ghirnikar, R S et al., Neurochemical Research 1998, 23(3):329-340; Norton, W T, Neurochemical Research 1999, 24(2): 213-218). This is a normal physiological reaction and is necessary for the healing process. In the case of a permanently anchored material in the tissue, the foreign body material may in addition induce a chronic inflammation that in the worst cases may jeopardize the function of the implant and the tissue. The material and the procedures related to the devices should therefore minimize chronic inflammation. Another complication that needs to be addressed is the reaction of the glial cells, particularly the astrocytes and microglia. In the event of perforating injuries to the central nervous tissue the astrocytes will proliferate and form an astroglial scar (Eng, F E et al., Neurochemical Research 2000, 25: 1439-1451; Polikov, V S et al., 2005, J Neuroscience Methods 148; 1-18)). Such a scar may form a capsule-like structure surrounding an implanted electrode and thereby insulate it from the rest of the central nervous tissue. In cases of a large astroglial capsule this may impair the function of the electrodes. Thus, the astroglial reaction needs to be controlled. It should not be totally prevented, however, since there are indications that lack of astrocytic involvement will actually cause a widespread inflammation and tissue reaction worsening the scenario (Eng, F E et al., Neurochemical Research 2000, 25: 1439-1451; Sofroniew, M V et al., Neuroscientist 2005, 11(5): 400-407). Microglia may also proliferate after an implantation. These cells have phagocytic capacity and they also release a number of substances that can trigger a chronic type of inflammation. By controlling the microglia the formation of the astrocytic capsule may be reduced. Besides being a health risk, the tissue reactions caused by different types of glia cells may impair the function of the implanted electrodes. For example, in case a zone devoid of neurons is created around the electrodes, or a scar is established, much higher current will be needed to activate living neurons. The increased current necessary to stimulate neurons at a distance may in turn cause further tissue damage through heat dissipation and/or through induction of irreversible reduction and oxidation reactions (see also U.S. Pat. No. 6,316,018)

4) The design of the multichannel electrode itself may also trigger delayed and long lasting tissue responses after implantation at least partly due to movements between electrode implant and the tissue. Of particular importance is the endogenous movements caused by breathing and by the heart beat. The consequent pulsatile movements are usually not uniform in the tissue. For example, the movement caused by the heart beat around a major artery propagates through the tissue in a nonuniform way. Movements between implant and tissue occurs if the implant is rigid or attached to a rigid structure that do not move along with the soft tissue in which the electrodes are implanted. It would therefore be an advantage to use flexible electrodes that after implantation are anchored in the tissue rather than in the skull or skeleton and that can follow the movements of the tissue and thereby avoid the friction between electrodes and tissue that otherwise may occur and which may trigger tissue responses. Movements between electrode and tissue can cause an unstable recording/stimulation situation and thereby impaired function of the implant. To reduce the movement between individual electrodes and the adjacent tissue caused by such endogenous movements, the electrodes should therefore be able to follow the tissue movements in all directions.

A further complication with multichannel electrodes used for research, in particular multichannel electrodes composed of numerous electrodes is that it is usually difficult or impossible to identify the neurones or cells recorded/stimulated by the individual electrodes. This hampers the interpretation of the results considerably since it is not possible to relate the recorded signals to cell type or cell morphology. This also may cause problems in interpretation of the effects of stimulation since it is not clear which cells were stimulated.

It would thus be a substantial advantage if the aforementioned complications could be avoided or at least alleviated.

OBJECTS OF THE INVENTION

An object of the invention is to provide a medical microelectrode, a bundle of microelectrodes or an array of microelectrodes or bundles of microelectrodes devoid of one or more drawbacks of microelectrodes, bundles of microelectrodes or arrays of microelectrode bundles known in the art.

Another object of the invention is to provide a method of studying the pharmacological effect of different concentrations of a drug on living tissue, in particular nervous tissue such as the brain.

Further objects of the invention will become evident from the following summary of the invention, a number of preferred embodiments illustrated in a drawing, and of the appended claims.

SUMMARY OF THE INVENTION

According to the present invention is disclosed a flexible medical microelectrode, a bundle of microelectrodes, and an array of microelectrodes and/or microelectrode bundles, comprising a means for releasing a drug and/or a gene vector into the tissue into which the electrode, the bundle or the array is inserted. In the following, the term "drug" is intended to also comprise "gene vector". The microelectrode of the invention, independent of whether a single electrode or comprised by the electrode bundle or the electrode bundle array of the invention, comprises an electrically conducting electrode body and an electrically non-conducting electrode matrix element stabilizing the electrode body during insertion into tissue. The electrode matrix element consists of or comprises a material dissolvable and/or degradable in the tissue, that is, in a body fluid. The means for releasing the drug and/or gene vector is the matrix or is comprised by the matrix of the invention, such as, for instance, particles distributed through the matrix of the invention or a portion of the matrix capable of forming an aqueous solution of the drug upon coming into contact with body fluid during the dissolution or degradation of the matrix. The particles may be drug particles or carrier particles comprising the drug, for instance microcapsules or porous or layered microspheres comprising the drug. It is also within the ambit of the present invention that the drug is linked to the matrix of the invention or to a particle distributed through the matrix of the invention by a bond that is cleaved, in particular hydrolytically or by the action of an enzyme, upon contact with body fluid. The drug or drug-containing particles may be distributed throughout the entire matrix element or portions of the matrix element, in particular portions of the matrix element surrounding an electrode tip. Their distribution may be evenly or so as to form a concentration gradient.

The microelectrode body of the invention comprises a distal electrode tip section including a sharp or blunt or even spherical tip, a main body section extending in a proximal direction from the tip section and, optionally, a proximal coupling section extending in a proximal direction from the main body section. "Distal" or "first" and "proximal" or "second" relates to the direction of insertion of the electrode into tissue with the electrode tip foremost. Upon insertion of the microelectrode of the invention into tissue, either as such or comprised by a bundle of electrodes or an array of electrodes or electrode bundles, and the dissolution or degradation of the electrode matrix element by body fluid and, in the case of an electrode bundle or an array of electrodes or electrode bundles, the (additional) dissolution of the bundle or array matrix or matrices by body fluid, an electrode of the invention is transformed into an microelectrode disposed in soft tissue. It is preferred for the electrode body, in particular its tip section, to comprise a means for anchoring the electrode body in the tissue, such as a hook.

It is preferred for sections of the electrode body to be insulated. Particularly preferred is an insulation scheme in which the main body section or a major portion thereof is insulated whereas the tip section is not insulated.

It is preferred for the diameter of the electrode body, in particular its main portion to be from about $10^{-7}$ m to about $10^{-4}$ m. Except for elements laterally extending from the electrode body, such as hooks for anchoring in tissue, it is preferred for the electrode main body section to have a uniform diameter. In particular, the main body section is circular in a transverse section. Preferably, the main body section is cylindrical or produced from a (cylindrical) metal wire by bending. Alternatively the main body section is preferably flat and rectangular in a transverse section; electrodes with flat thin body sections can be produced, for instance, by lithographic etching techniques applied to a thin layer of metal on an electrically insulating support. Alternatively flat thin body sections, which may consist of one or more electrically conducting layers and one or more electrically insulating layers, can be cut out by, for instance, laser cutting, from a correspondingly layered sheet of material. It is also possible for each of such layers to be composed of electrically conducting portions and electrically insulating portions. Other geometries than those aforementioned are however not excluded from the invention.

According to a preferred aspect of the invention the microelectrode body lacks a proximal coupling section, the main body section being integral with an electric conductor for establishing electrical contact between the electrode body and an electrode control unit. Preferably the electrode body and the electrical conductor are of same material, such as of a thin metal wire of a good electrical conductor. In absence of a proximal coupling section the nominal length of the electrode body of the invention is its embedded length in the electrode matrix. In the embodiment lacking a proximal coupling section the proximal end of the electrode body is defined by the proximal end of the matrix.

In use, the electrode of the invention, independent of whether used as a single electrode or being comprised by an electrode bundle or an array of electrodes or electrode bundles, is electrically coupled to a control unit. The control unit of the invention feeds an electric current to the electrode and/or detects an electric current or an electric potential transmitted by the electrode, the current or potential arising in the tissue to which it is inserted. The control unit of the invention comprises a microprocessor and control software stored in memory of the microprocessor.

The control unit of the invention can be disposed internally or externally of the person or animal provided with an electrode, an electrode bundle or an array of electrodes or electrode bundles of the invention. It can be in electrically conducting contact with an electrode of the invention by means of an electrically conducting lead or it can be in contact by radiative means. It is also possible for the control unit to be integrated with an electrode of the invention in form of a minute microprocessor disposed at a proximal portion of the electrode body, the electrode bundle or the array of electrodes or electrode bundles. The microprocessor may record an electric current or potential arising in the soft tissue near an electrode tip and store the record in a memory, which can be read, for instance, after withdrawal from tissue.

The present invention is furthermore based on the insight that administration of a tissue protecting drug to the tissue surrounding the inserted electrode may benefit the use of the electrode.

In addition, the present invention is based on the insight that administration of a drug other than a tissue protecting drug to the tissue surrounding the inserted electrode may benefit the use of the electrode.

Drug administration through an electrode of the invention is not restricted to one drug. It is also possible to administer two or more drugs simultaneously or sequentially. The two or more drugs may be located in a single electrode matrix element or in different compartments or portions of an electrode matrix element, the compartments being constituted by a single matrix material or by different matrix materials. If the matrix element of the invention comprises two or more compartments, they can advantageously be disposed in rotationally symmetric layers extending along the electrode body or a portion thereof or in adjacent matrix sections each extending along a portion of the electrode body. By embedding single electrodes, bundles of electrodes and arrays of electrodes or electrode bundles in a solid electrode matrix that is dissolvable or degradable in body fluid, even electrodes with very delicate electrode bodies, such as electrode bodies in the micrometer or even nanometer range, can be inserted into tissue in good condition. One purpose with arranging the electrode matrix element of the invention thus is to provide for insertion of the electrode, the bundle of electrodes, and the array of electrodes or electrode bundles of the invention into tissue while protecting the integrity of the electrode body and tip, and if present, of tissue retaining elements, such as hooks, extending from the electrode tip or body. For easy insertion, the electrode matrix element is preferably narrowing in a distal direction. At its distal end the electrode matrix element has preferably the form of a blunt or sharp tip. The tip may be conical or about conical but may also be flattened. In contrast, a matrix enclosing a plurality of electrodes or electrode bundles of the invention so as to form an array of electrodes or electrode bundles, which electrodes or electrode bundles comprise and are already embedded in one or more electrode matrix elements, is termed array matrix element.

A preferred axial length, that is, a length in the intended direction of insertion of the electrode into tissue, of the electrode and/or the electrode matrix, the electrode bundle and/or the electrode bundle matrix, the electrode array or electrode bundle array and/or and the corresponding matrix is 100 mm or less or 50 mm or even 15 mm or less. Exceptionally, the axial length of any of said electrodes, electrode arrays, electrode bundles and/or corresponding matrices is more than 100 mm.

Most important, the electrode matrix element of the invention is not a thin coat on the electrode body but is an element physically stabilizing the electrode body including its tip and, if present, tissue retaining elements during insertion into tissue and for a desired period of time after insertion. The electrode matrix element of the invention enclosing and stabilizing an electrode or an electrode bundle is preferably rotationally symmetrical. A preferred shape is that of a minuscule projectile with a pointed tip and a flat rear base. It is preferred for the electrode matrix element to be disposed rotationally symmetrical in respect of the electrode or electrode bundle, sharing its longitudinal axis with that of the electrode body or electrode bundle. Accordingly, the electrode matrix element of the invention is preferably circular or elliptical in a section transverse to its longitudinal axis. According to the invention it is preferred that a transverse diameter or short ellipse diameter of the electrode matrix of the invention is substantially larger than the diameter of an electrode body enclosed by it, such as larger by a factor of 2, 5, 10, and even 25 or more.

According to the invention, it is important that the combination of a) an electrode, an electrode bundle, or an array of electrodes or electrode bundles, and b) one or several matrix elements has sufficient physical stability or rigidity to allow it to be inserted into soft tissue along a generally straight path, which is opened up by the action of the respective tip on the tissue. The tip thus cuts into the tissue. This method of placing the electrode, the bundle of electrodes, the array of electrodes or of bundle of electrodes of the invention at a desired location in soft tissue is substantially different from implantation, which would require opening up the path by surgery. If not supported by the matrix element(s) the electrode, the electrode bundle or the array of electrodes or electrode bundles could not be inserted into tissue due to insufficient rigidity causing the device to be inserted to bend and thereby to deviate from the desired insertion path.

According to a preferred aspect of the invention, the surface of the matrix is provided with a layer of material facilitating insertion, such as a material of low friction in contact with soft tissue. On the other hand, the insertion facilitating layer should readily dissolve and/or being degraded upon insertion. A preferred insertion facilitating layer may comprise or consist of a lipid having a melting point a few degrees higher than the temperature of the tissue into which is intended to be inserted, such as a melting point of 40° C. to 43° C. Additionally or alternatively the layer on the surface of the matrix may be designed to substantially delay dissolution and/or degradation of the matrix, such as by 1 min or 10 min or more. A suitable layer of this kind can be formed by polymers used for tablet coating in the pharmaceutical industry for slow release in an aqueous environment of about pH 7-7.5.

According to a preferred aspect of the invention, the electrode body is fully enclosed by the electrode matrix element except for at its proximal end, the electrode tip being disposed at a distance in a proximal direction from the tip of the electrode matrix.

According to another preferred aspect of the invention it is desirable for the electrode body of the invention to have, once implanted, freedom of movement of portions thereof not only in a lateral direction but also in a longitudinal direction, independent of whether pertaining to a single electrode or of an electrode comprised by an electrode bundle or by an electrode bundle array. Thereby negative effects of non-uniform movements of surrounding tissue on the electrode body are avoided, in particular effects tending to dislocate the electrode body and/or to make it move in a manner damaging surrounding tissue. What is said herein about the freedom of movement of the electrode body relates to an electrode body in the tissue upon dissolution and/or degradation of the electrode matrix, that is, once the electrode body is no longer constrained in its movement by the electrode matrix element. In particular, the present invention is based on the insight that it is advantageous for such an electrode body to comprise portions capable of movement relative to each other so as to increase or decrease their distance along the electrode. The invention is also based on the insight that, for their implantation or insertion, in particular their implantation or insertion in a desired configuration, the electrode body of the invention, independent of whether pertaining to an electrode bundle or an array of electrode bundles or an array of single electrodes and electrode bundles or not, does require configurational stabilization. In this application, "configuration" relates to the three-dimensional forms or states that an electrode of the invention can assume or be forced to assume due to its flexibility. According to the invention configurational stabilization is provided by at least partial embedment of the electrode in the electrode matrix element, which is removed by dissolution in body fluid or by degradation once the electrode has been disposed in a desired location in soft tissue. Thus the electrode matrix or electrode support material is one that is dissolvable or degradable in body fluid, that is, in an aqueous environment but also, if the electrode is inserted into fatty tissue, in an environment rich in fat. After dissolution or degradation the electrode matrix material or degradation products thereof, respectively, is cleared from the insertion site by solute transport mechanisms operating in living tissue and/or is metabolized. The electrode matrix element of the invention may be of a material that must to be degraded to make it soluble or to enhance its solubility in body fluids; such degradation is effected by mechanisms operative in living tissue and/or by adjuvant, such as an enzyme, comprised by the electrode.

According to the present invention is thus disclosed a medical microelectrode for insertion into soft tissue, comprising an electrically conducting elongate electrode body having a first, proximal end and a second, distal end, the electrode body comprising a tip section extending from its distal end, a main body section extending in a proximal direction from the tip section, and, optionally, a coupling section extending in a proximal direction from the main body section, wherein the tip section, the main body section and, optionally, the coupling section are embedded in a first electrode matrix element, which is substantially rigid, biocompatible and soluble or biodegradable in a body fluid, further comprising one or both of: a dissolution retarding layer on the first electrode matrix element; a second electrode matrix element, which may optionally comprise two or more sections, disposed between the first electrode matrix element and the electrode; wherein a drug capable of being released upon dissolution or biodegradation of the first electrode matrix element is comprised by the first electrode matrix element or the second electrode matrix element. The drug can be dispersed or dissolved in the matrix or be comprised by the matrix in microencapsulated form or comprised by a rod of biodegradable material or a material dissolvable in body fluid.

In a preferred embodiment the microelectrode comprises an anchoring means disposed at the tip section.

In another preferred embodiment the electrode body comprises a non-conducting core, one or more electrically conducting layers on the core, an insulating layer on the one or more electrically conducting layers and, optionally, one or several passages through the insulating layer perpendicular to the core permitting electrical contact with the electrically conducting layer(s).

It is preferred for the tip section, the main body section and, if present, the anchoring means to be fully embedded in the first electrode matrix element.

In a preferred aspect of the invention the first electrode matrix element comprises two or more sections differing in their dissolution or degradation rate.

A preferred diameter of the electrode body is from about $10^{-7}$ m to about $10^{-4}$ m.

According to another preferred aspect of the invention the main body section comprises portions capable of movement relative to each other upon dissolution or degradation of the first electrode matrix element, so as to increase or decrease their distance along the electrode body.

According to a further preferred aspect of the invention the first electrode matrix element comprises a first drug and the second electrode matrix element comprises a second drug.

Furthermore, according to the present invention, is disclosed a medical microelectrode bundle comprising two or more electrodes of the invention with their electrode bodies disposed substantially in parallel and sharing said first electrode matrix element or comprising a bundle matrix element enclosing said first matrix elements. According to a preferred aspect of the invention the microelectrode bundle comprises a dissolution retardation coating on the shared first electrode matrix element or on the bundle matrix element. It is preferred for the proximal ends of the two or more electrodes of the bundle to be disposed in substantially the same plane. According to another preferred aspect of the invention the microelectrode bundle comprises, in addition to the shared first electrode matrix element or the bundle matrix element a bundling means disposed at or near the proximal ends of the electrodes, which bundling means does not comprise a dissolvable or biodegradable matrix. The microelectrode bundle of the invention may comprise one or more optical fibres. According to a further preferred aspect of the invention two or more first or second electrode matrix elements of a microelectrode bundle comprise different amounts of a drug or differ in their drug release properties. Insertion of the microelectrode bundle of the invention into soft tissue is facilitated by use of a bundle insertion element such as a rod. For such use the microelectrode bundle of the invention is provided with a releaseable coupling means.

Furthermore, according to the present invention, is disclosed an array of medical microelectrodes or microelectrode bundles comprising two or more microelectrodes of the invention or two or more microelectrode bundles of the invention, wherein the two or more microelectrodes or two or more microelectrode bundles are disposed interspaced on a face of a solid support. It is preferred for the two or more microelectrodes or two or more microelectrode bundles of the array to be embedded in a substantially rigid biocompatible array matrix element, which is soluble or biodegradable in a body fluid. Preferably the dissolution or degradation rate of the array matrix element in said body fluid is higher than the dissolution or degradation rate of said first electrode matrix element or bundle matrix element. The array matrix element may additionally comprise a dissolution or degradation retardation coat on the array matrix element.

Single Electrodes

The microelectrode body, which is preferably about circular or elliptic in cross section, comprises an electrically conducting or non-conducting core, an electrically conducting layer on the core if the core is non-conducting, and an insulating layer on the electrically conducting layer or core. However, other electrode bodies with other cross sections, such as rectangular or polygonal, may also be used. Alternatively, the electrode body comprises or consists of a non-conducting polymer tube filled with an electrically conducting material. A non-conducting core is preferably a natural, semi-synthetic or synthetic polymer filament, such as a filament of silk, cotton, artificial silk (cellulose acetate), polyethylene, polypropylene, polyamide, etc. A conducting core is a thin metal wire of, for instance, gold, platinum, titanium, iridium, an alloy comprising the aforementioned or other metals, stainless steel or an electrically conductive polymer fibre. The electrically conducting layer on a non-conducting core consists or comprises a metal of high electrical conductivity, such as silver, gold and or a suitable metal alloy, e.g. platinum-iridium, deposed on the core by, for instance, ion sputtering or evaporation techniques. In case of a gold layer adhesion to the core can be improved by interposition of a chrome or tungsten layer between the gold layer and the core. Such interposition is also feasible with other metal layers. The thickness of a deposed metallic conductive layer is from 0.1 μm to about 100 μm. Alternatively, the electrically conducting layer may consist or comprise an electrically conducting polymer. The insulating layer comprises or preferably consists of an electrically non-conducting polymer. In most applications, the diameter of the electrode body is from about $10^{-7}$ to about $10^4$ m, preferably less than about $2.5 \cdot 10^{-5}$ m. However, in some applications the electrode body may have a larger diameter, in particular if the electrode is intended for producing lesions of soft tissue.

The insulation layer of the electrode body extends preferably from the body's proximal end to the body's distal end, that is, the entire electrode body is insulated. Examples of materials suitable for insulation are glass, polyvinyl formal, epoxy resin, poly(p-xylylene), polyamide, silicone rubber or a water-resistant lacquer. It is however possible to provide along the electrode body passages through the insulation layer to the conducting core, in particular passages disposed about perpendicular to the core.

If electrical stimulation of a larger volume of tissue is intended, it may be preferred not to insulate the portion of the electrode body intended for insertion into the target tissue. Alternatively, the electrode body may comprise regions that are not insulated to allow stimulation/recordings of multiples sites within the tissue.

To facilitate insertion into tissue the electrode body of the invention is at least partially embedded in a rigid or substantially rigid element or body of a biocompatible matrix material termed electrode matrix element. The electrode matrix material is preferably macroscopically uniform. The embedment comprises at least a portion of the electrode body, more preferred the electrode tip and a portion of the electrode body extending from the tip. "Substantially rigid" indicates that the body may be only slightly resiliently flexible. The electrode matrix element or body comprises or consists of a solid matrix material that is soluble or biodegradable in a body fluid, in particular an aqueous body fluid but, alternatively, also in one rich in fat. Incorporation of the electrode in the matrix body not only allows the electrode to be inserted or implanted into tissue and to be disposed therein in a desired disposition but also in a desired configuration. The electrode body or at least portions thereof may be configurationally locked in the electrode matrix element. After dissolution or degradation of the electrode matrix element the electrode body may retain its initial or first configuration in tissue or assume or made to assume a second configuration or an unlimited number of configurations. By "initial configuration" is meant the configuration of the electrode or the electrode body or a section of the electrode body embedded in a matrix. A curvy or other non-straight shape of the electrode body improves the anchoring of the electrode in tissue, since tissue cells will grow close to the body. In contrast to a straight electrode body, a curvy or other non-straight electrode body does improve the ability of the electrode of the invention to move, without being dislocated, in unison with non-uniform movements of the tissue into which the electrode is implanted or inserted. According to an important aspect of the invention the matrix body comprises a drug or gene vector capable of release to a body fluid, in particular an aqueous body fluid, upon implantation of the electrode. The drug may be released from the matrix body prior to its the dissolution or degradation, in particular at least partially. The drug may be comprised, for instance, by a matrix of open structure, such as a matrix provided with open microchannels. The drug may be released from the matrix concurrently with the dissolution or degradation of the matrix. The drug can be present in the matrix in a dispersed or dissolved state, in a state adsorbed to the pore walls of a porous matrix and even as a prodrug linked by a covalent bond to the matrix. Alternatively the drug can be present in the matrix in microencapsulated form or comprised by a body, which dissolves in a body fluid or is biodegradable in human tissue.

Exceptionally, the drug can be comprised by a body separate of the electrode matrix element, which body is can be either dissolvable in a body fluid or not, or can be biodegradable or not. The drug is preferably one that protects from damage the tissue into which the electrode is inserted and/or assists the recovery of damaged tissue. Independent thereof, the drug of the invention is a drug exerting a pharmacological effect on tissues adjacent to the inserted electrode, in particular nerve tissue, most particularly tissue of the nuclei or white matter of the brain and the spinal cord.

In the embodiment of the electrode body and thus the electrode of the invention having a configuration permitting the distance from its proximal end to its distal end to be increased and/or decreased once implanted in human or animal tissue, the adoption of a second configuration by the electrode body can be provided by several means. If the electrode body is resiliently flexible or comprises resiliently flexible portions it may be embedded in the electrode matrix element in a compressed or tensioned state so that, upon dissolution of the electrode matrix element after implantation of the electrode in tissue, the electrode body may expand or contract, respectively.

In its initial configuration the electrode body, while generally substantially extending in one direction, may be straight or comprise regular or irregular bends, spirals, loops, zigzag sections, etc. In other words, in its initial conformation, the length of the electrode body may be substantially greater than the distance between its proximal and distal ends. By substantially greater is meant a length such as by 2 percent or more, in particular by 5 percent or more, even by 20 percent or more, and up to by 50 percent or more, of the distance between its first and second electrode ends. The tip section of the electrode extending from the second, distal end however preferably has a straight or only slightly bent configuration.

The distal end or tip section of the electrode, which is not insulated, can be of any suitable shape. Sharp tips are particularly advantageous if the electrode is intended for recording purposes. If the electrode is intended to be used for stimulation it is preferred that the electrode tip section does not comprise sharp edges but rather has a smooth contour to reduce the erosion of the tip section. Optionally the surface area of the electrode tip section may be enlarged by roughening to increase the contact with surrounding cells and decrease the impedance of the electrode. A rough surface can be obtained by, for instance, coating the electrode with platinum black or by etching.

At its proximal end, the electrode body is in electrically conductive contact with electronic equipment via an insulated flexible electrical wire.

The tip section and/or the main body section the electrode of the invention can be provided with anchoring means, such as rough surface portions or surface portions promoting adhesion to surrounding tissue. Electrode body sections capable of adhering to adjacent tissue may even be of a kind, for instance of titanium or having portions coated with titanium oxide, allowing tissue adhesion or ingrowth. Thin laterally extending filaments attached to the tip section, which are disposed in a proximal direction during the insertion procedure and then unfold on retracting the electrode for a short distance, are known (WO 2007/040442); the electrode of the invention may be provided with such filaments to anchor it in human or animal tissue. It is preferred that these thin laterally extending filaments have a diameter equal to or preferably less than the diameter of the electrode body, and/or to be of a length to allow them to laterally protrude for a suitable distance, such as up to fifty µm or more, and even up to hundred µm or more, from the electrode. It is preferred for the laterally extending filament(s) to additionally function as electrodes, in which case at least their tip is not insulated. It is also preferred for a laterally extending filament to comprise or consist of the electrically conductive material of the electrode, and for that material to be integral with the material of the electrode body. It is however also within the scope of the invention that the lateral extending filaments are of a material different from that of the electrode. Since laterally extending filaments do not hinder insertion of the matrix-embedded electrode into tissue due to them being enclosed by the electrode matrix, they may extend from the electrode in any direction, such as a distal, radial or proximal direction. It is also possible for an electrode to comprise a multitude of laterally extending filaments and for those filaments to extend in one or several directions from the electrode. Likewise, it is preferred for the core or supporting tube of the electrode to be of the same material as the tip section and to be integral with it. In an electrode equipped with protruding elements at its tip section such withdrawal may allow the protruding elements to become anchored in the tissue and to make the electrode resist withdrawal. Pushing an electrode of appropriate tip design, such as a tip bending or slanting away from the long axis of the electrode body defined by the straight line connecting its first and second ends further into the tissue may cause its tip portion to deviate sideways from the direction of the long axis.

The electrode of the invention is intended for insertion into soft living tissue, in particular brain and spinal cord tissue, but also, for instance, into the liver, the kidneys, skeletal muscles, heart muscles, visceral muscles, and connective tissue. The electrode of the invention can be used for recording and/or for nerve-stimulating purposes. If used for recording purposes, an electrode wire of the invention can be equipped with a miniaturized preamplifier. It is preferred for the amplifier to be arranged at a short distance from the tip, such as at the junction of the body and tip sections, to improve the signal to noise ratio.

To further facilitate insertion into soft tissue, it is preferred that a micro-manipulator rod or similar is attached to the matrix or embedded in the matrix near or at the proximal end thereof. Releaseable attachment of the micro-manipulator may alternatively be provided by a docking means comprised by the proximal coupling section of the electrode.

Electrode Bundles

In certain applications it is an advantage to use multiple, suitably arranged electrodes of the kind disclosed above.

The combination of two or more electrodes of the invention in a common or shared matrix body is termed electrode bundle. The shared matrix forms an electrode bundle matrix element. It is soluble or biodegradable in a body fluid. An important feature of the electrode bundle of the invention is that at least two electrodes comprised by the bundle have to be electrically insulated from each other. It is though preferred for all or substantially all electrodes of the bundle to be electrically insulated in respect of each other. The bundle matrix element is rigid or substantially rigid. The purpose of the bundle matrix element is to impart physical stability to the electrode bundle so as to allow it to be inserted into tissue along a substantially straight path. This allows disposing a plurality of electrodes in a desired soft tissue region. It is also within the ambit of the invention to provide an electrode bundle with conventional straight electrode wires, optical wires, contractile polymers or stiff electrode chips containing electrodes and/or electronics, which elements are at least partially disposed in the matrix body. Optionally, the electrode or bundle matrix element comprises two or more sections of matrix materials differing in their dissolution rate in an aqueous environment. A sectioned matrix element for an electrode bundle of the invention corresponds in respect of its features to the electrode matrix element of the invention described above. In addition to the shared electrode bundle matrix element of the invention one or more electrodes of the bundle, in particular all electrodes of the bundle, may be provided with an electrode matrix element of the invention; in such case the electrode bundle matrix element joins or even may enclose the one or more electrode matrix elements of the bundle It is preferred for electrode bodies comprised by an electrode bundle of the invention to be of varying length and, if the electrode bundle matrix element or body is of rotationally symmetric form, for instance cylindrical, to be symmetrically arranged in respect of the central axis thereof. It is preferred for the longest electrode bodies to be disposed at a short distance from the central axis and for the shorter ones at a greater distance from the axis so as to make the totality of their tips reflect the form of the matrix tip. Their proximal ends are preferably disposed in or near a plane transverse to the rotational axis. It is however also within the scope of the invention to arrange the electrode bodies in a manner forming a unilaterally slanting or otherwise not symmetric electrode bundle tip. Thus the electrode bundle matrix element may be tapering in a distal direction so as to form, for instance, a conical or flat triangular terminal distal portion. The terminal distal portion of the electrode bundle matrix element can have a blunt shape to minimize the risk of vascular rupture during insertion of the electrode bundle into soft tissue.

According to another preferred aspect of the invention the electrode bundle comprises one or more optical fibres to allow radiative stimulation of the tissue or components thereof and/or for recording radiation emanating from surrounding tissue. In a manner corresponding to that of the electrode bodies the one or more optical fibres are kept in a selected position in the electrode bundle by means of the electrode bundle matrix element.

According to a further preferred aspect of the invention two or more electrode bodies in the matrix-embedded electrode bundle of the invention can be joined at or near their first ends by a base plate of, for instance, a ceramic or polymer material. Electrodes so joined may be of same or different length. The base plate may be equipped with electronic components such as amplifiers and be connected to electronics outside the tissue for stimulation and recording purposes via a cable or telemetrically; it may also be used for mounting a means for receiving a micromanipulator.

According to a still further preferred aspect of the invention the electrode bundle comprises one or more contractile bimetallic elements capable of changing their shape, for instance to bend, when electric current is passed through them. Such contractile elements can be used to control the insertion path of the matrix-embedded electrode bundle.

For insertion of the electrode bundle of the invention into soft tissue a micromanipulator is attached or attachable to a proximal end portion of the electrode array, from which it extends in a proximal direction.

The stiffness of the electrode bundle of the invention provided by the electrode matrix shared by the bundle electrodes facilitates its insertion into tissue. Upon insertion, the electrode matrix may be quickly or slowly dissolved or degraded. A desired dissolution or degradation rate can be selected by using an appropriate matrix material. Thereby the electrode body becomes capable of lateral displacement in respect of neighbouring electrode bodies.

Arrays of Electrodes and/or Electrode Bundles

According to the invention two or more matrix-embedded electrodes and/or electrode bundles disposed in parallel or about in parallel can be joined by a substantially solid array matrix or glue that can dissolve in or be degraded by an aqueous medium such as a body fluid but also in a body fluid rich in fat such as nerve tissue. The array matrix must be biocompatible. Suitable materials include glues on a carbohydrate or a protein basis, such as alkylated and/or carboxylated cellulose derivatives, amylose, and gelatin, but can also be of a different nature, such as polyvinyl alcohol, polyvinylpyrrolidone, and alkali salts of polyacrylic acid. In this manner electrodes and/or electrode bundles can be arranged in an array in a desired geometric pattern suitable for implantation. Thereby the time required for implantation is considerably shortened compared with that for the same geometric pattern obtained by implantation of individual electrodes and/or electrode bundles. One or more matrix-embedded electrode bodies and/or electrode bundles of the invention in such an array can be substituted by two or more of matrix-embedded electrode bodies of the invention that are temporarily or permanently kept in a fixed relationship in respect of each other. The means for keeping them in such fixed relationship may comprise or consist of one or more matrix materials of the invention or be independent thereof. If independent thereof, the means can be one that dissolves and/or disintegrates more slowly in an aqueous environment than any other matrix material of the matrix-embedded electrode bundle or a permanent one, such as a means keeping the electrode bundle of WO 2007/040442 in a fixed relationship. Similarly one or more electrode bundles in the electrode array of the invention can be substituted by one or more electrode bundles of WO 2007/040442. A suitable distance between electrode bundles in an electrode bundle array of the invention is from 50 μm to 500 μm or more. In one embodiment, individual matrix embedded electrode bodies of an electrode bundle of the invention are mounted in a interspaced configuration with their proximal ends secured in a base plate that is dissolvable in an aqueous body fluid. This arrangement facilitates insertion into tissue of the bundle or of an array comprising two or more of such bundles.

The array of matrix-embedded electrode bundles or of a combination of matrix-embedded electrodes of the invention and matrix-embedded electrode bundles of the invention is suitable for long-lasting stimulation, multi-channel recordings of electrical neuronal activity and levels of transmitter substance or other bioactive molecules through measurements of redox reactions and precise lesions of the tissue for scientific, medical and animal care purposes.

According to the present invention a preferred means for drug release is a matrix element. A drug is embedded in the matrix by dissolution, dispersion, linkage via a biodegradable linker or by any other suitable manner.

Another preferred means for drug release is a compartment such as a microsphere or other microparticle dispersed in the matrix.

A further preferred means for drug release is an electrode coating comprising the drug, the electrode coating being enclosed by the matrix.

The drug of the invention includes but is not limited to an agent affecting physiological and/or pathological processes in the tissue into which the electrode, the electrode bundle or the array of electrode bundles of the invention is inserted.

The array matrix element or body of the invention is of a biocompatible material that dissolves in an aqueous environment such as body fluids. Prior to dissolving, it may swell or not. The array matrix element is preferably oblong in a distal direction, that is, forms the frontal part of the matrix-embedded electrode that is first introduced into the tissue. It can be shaped, for instance, as a bar of a length at least equal to the distance between the first and second ends of the electrode in its initial conformation. The array matrix element is preferably tapering in the direction of its distal end. Its distal end section is preferably about conical to facilitate insertion into soft tissue. Its distal tip may have a sharp or a blunt shape. A blunt shape minimizes the risk of vascular rupture during insertion while a sharp tip will reduce the resistance of the tissue against insertion. The shape of the array matrix element permits to follow a straight insertion track line when inserting the electrode deep into the soft tissue, and thereby enables the user to accurately position the electrodes of the array in the tissue. A wettable matrix will also constitute a slippery surface minimizing strain forces in the tissue, longitudinally along the sides of the array matrix element.

To permit, in animal studies, rapid screening of effective drug concentrations or screening of an effective drug release time course, individual electrodes or electrode bundles of an array of electrodes or of electrode bundles, respectively, can be embedded in one and the same matrix element containing one drug in one concentration; alternatively two or more of such individual electrodes or electrode bundles can be embedded in two or more matrix elements, respectively, the matrix containing a corresponding number of concentrations of said one drug or a corresponding number of different drug in the same concentration or in different concentrations. By this arrangement screening of different concentrations of one drug or of different drugs can be carried out by use of one array of this kind. It is also possible to coat the matrices of two or more electrodes or electrode bundles intended for incorporation into an array with a corresponding number of coatings differing in their barrier properties against humidity, thus more or less delaying the degradation or dissolution of matrices so protected.

According to preferred embodiment of the invention, in an matrix element comprising two or more sections, the sections may be arranged so that there is one outer section fully or partially enclosing one or more inner sections in which an electrode of the invention is embedded. The drug or drugs intended for release are only comprised by the inner section(s). The inner matrix element section(s) are preferably not enclosing the electrode tip while the outer section encloses the tip as well as the inner sections. The outer section thus is intended primarily for protecting the physical integrity of the electrode during insertion into tissue, and has a dissolution or degradation profile substantially different from that of the inner section(s), that is, is dissolved and/or degraded substantially more readily than the inner matrix section(s), such as by a factor of 5, 10 or even 100.

According to a further preferred embodiment of the invention the distance between the tips/distal ends of electrodes in electrode bundles or in arrays of electrode bundles after dissolution or degradation of the matrix or matrices enclosing them should be at least 200 µm or more, preferably 500 µm or more. This final implantation distance is obtained by unfolding of the electrodes in a bundle by means of a plug of water-swellable polymer material disposed in the centre of an electrode bundle, that is, with the electrodes of the bundle surrounding it. Alternatively or additionally, the final implantation distance is obtained by using electrodes with a main body section incorporated in a matrix in an axially compressed and/or radially bent state. Upon degradation and/or dissolution of the matrix they are returning to their original uncompressed and/or non-bent state.

Matrices

Polymers which can be used for forming the matrix include ones that can be dissolved and cured or polymerized on the medical device or polymers having relatively low melting points that can be blended with therapeutic agents. Such biocompatible polymers known to the art include, but are not limited to: gelatine, collagen, gum Arabic, polyglycolic acid, carboxyvinyl polymer, sodium polyacrylate, carboxymethyl, sodium carboxymethyl cellulose, pullulan, polyvinylpyrrolidone, karaya gum, pectin, xanthane gum, tragacanth, alginic acid, polycarbonates, polyoxymethylenes, polyimides, polyethers, cellulose, cellulose acetate, cellulose butyrate, cellulose 65 acetate butyrate, cellulose nitrate, cellulose propionate, cellulose ethers, carboxymethyl cellulose collagens, chitins, polylaetic acid, polyglycolic acid, and polylaetic acid-polyethylene oxide copolymers, polyamides, polyorthoesters, polyanhydrides (PAN), polycaprolactone (PCL), maleic anhydride copolymers, polyhydroxybutyrate copolymers, as well as mixtures and blends thereof. Examples of the above include, but are not limited to, poly 1,3-(bis(p-carbophenoxy)propane anhydride ((PCPP) an aromatic polyanhydride), polymer formed from the copolymerization of pCPP with sebacic acid (i.e., a copolymer of an aromatic diacid and an aliphatic diacid) and polyterephthalic acid (i.e., polyterephthalic anhydride, and aromatic anhydride), poly(L-lactide) (PLLA), poly(D,L-lactide), (PLA), polyglycolide(PGA), poly(L-lactide-co-D,L-lactide) (PLLAJPLA), poly(L-lactide-co-glycolide)PLLN-PGA), Poly(D,L-lactide-co-glycolide)(PLAJPGA), poly (glycolideco-trimethylene carbonate) (PGNPTMC), polyethylene oxide (PEG), polydioxanone (PDS), polypropylene fumarate, poly(ethyl glutamate-co glutamic acid), poly(tert-butyloxy-carbonylmethyl glutamate), polycaprolactone (PCL), polycaprolactone co-butylacrylate, polyhydroxybutyrate (PHBT) and copolymers of polyhydroxybutyrate, poly(phosphazene), poly(D,L-lactide-co-caprolactone) (PLN PCL), poly(glycolide-co-caprolactone) (PGAJPCL), poly(phosphate ester), poly(amino acid) and poly(hydroxybutyrate), polydepsidpeptides, maleic anhydride copolymers, polyphosphazenes, polyiminocarbonates, poly[97.5% dimethyl-trimethylene carbonate)-co-(2.5% trimethlyene carbonate)], cyanacrylate, polyethylene oxide, hydroxypropylmethylcellulose, polysaccharides such as hyaluronic acid, chitosan and regenerate cellulose, Poly (ethylene-co-vinyl acetate) (EVA); isobutylene based copolymers of isobutylene and at least one other repeating unit (e.g., butyl acrylate, butyl methacrylate, substituted styrenes (e.g., amino styrenes, hydroxy styrenes, carboxy styrenes, sulfonated stryenes, etc.) homopolymers of polyvinyl alcohol, copolymers of polyvinyl alcohol and at least one other repeating unit, such as a vinyl cyclohexyl ether, hydroxymethyl methacrylate, hydroxyl or amine terminated polyethylene glycols, etc.), acrylate based copolymers (e.g., methacrylic acid, methacrylamide, hydroxymethyl methacrylates, etc.), ethylene vinyl alcohol copolymers, silicone based copolymers of an aryl or alkyl siloxane and at least one repeated unit (e.g., butyl acrylate, butyl polymer, (e.g., a copolymer of butyl methacrylate and PEG). (US 2005/0187146 A1).

Preferred materials may vary depending on the type of application and examples are listed in the sections describing different embodiments of the invention.

Bioactive and biocompatible polymers may be combined non-covalently to form polymer blends and covalently to form interpenetrating polymer networks, copolymers and graft polymers. Preferred combinations of bioactive and biocompatible polymers include, but are not limited to, polyurethanes, heparan sulfate and RGD peptides, polyethylene oxides, chrondroitin sulfate and YIGSR peptides, silicone polymers, keratan sulfate and VEGF biomimetic peptides, SIBS, perlecan and IKVAV peptides and N-butyl methacrylate, heparin and fibrin fragments.

Optionally, the electrode or array matrix of the invention comprises two or more sections of matrix materials differing in their dissolution rate in an aqueous environment. For example, in certain applications it is advantageous for the matrix to comprise or consist of two sections, a proximal section and a distal section, wherein the dissolution rate of the material of the distal section is substantially higher than that of the material of the proximal section, so as to shorten the dissolution time of the distal section by from one to ten minutes. This design enables the electrode of the invention to be inserted close to the target tissue with both matrix sections intact; upon dissolution of the matrix material of the distal section, in which a distal or second end portion of the electrode body and/or the tip section is embedded, the electrode may be pulled back in the tissue by a short distance or pushed further into the tissue by a short distance.

It is within the ambit of the invention for a matrix of the invention to comprise a dissolution enhancing means such as channels that can be infiltrated by body fluid. Thus the matrix body or a portion thereof may have non-porous or a porous structure.

It is also within the ambit of the invention to provide the matrix with a means for retarding dissolution. Retardation of the dissolution of the matrix material can be achieved by arranging one or more layers of dissolution retardation coating on the matrix body or sections thereof. The matrix dissolution retardation coating is of a material that dissolves in an aqueous environment at a rate substantially slower that of the matrix body or a matrix body section protected by it.

The matrix dissolution retardation coating may also be one that is not readily dissolvable but is degradable in an aqueous environment, such as a polyester coating, for instance a polyglycolate, polylactate, poly(glycolate, lactate) or polycarbonate coating or a peptide coating, such as a coating of collagen.

According to another preferred aspect of the invention the provision of an outer layer of a material that reduces friction in respect of the tissue during the implantation is preferred. An outer layer or coat of a low friction material may reduce injury caused by the implantation procedure. It may also reduce the risk of carrying with it cells, such as meningea fibroblasts, from a superficial tissue to a deeper tissue during electrode implantation. Suitable coat materials include polyvinylalcohol, collagen, chitin, agar, hyaluronic acid, cf U.S. Patent Application No. 2008234790 A1 incorporated herein by reference.

Drugs

According to the present invention, any drug or combination of drugs of interest may be administered to soft tissue via the electrode and/or array matrix of the invention. Preferred drugs according to the invention include drugs for treatment of bleeding, infection, and inflammation. Drugs reducing or preventing encapsulation by scar formation and preventing cell death are also preferred. According to the invention the drug is released into the tissue adjacent to an electrode body. According to a preferred aspect of the invention the drug is embedded in a separate biocompatible material forming a coat on an electrode or one or several electrode bodies of an electrode bundle. The electrode or array matrix may be applied in one or several layers. For instance, only one of several layers may contain a drug or two or several layers of a coating may contain different drugs. By providing electrodes coated in this manner in an electrode bundle or array of electrode bundles, different drugs may be released in the vicinity of selected electrodes of the invention. Drugs may also be comprised by microspheres or other types of microparticles embedded in the matrix, and may be released from the microspheres and microparticles upon dissolution or degradation of the matrix concurrently or subsequently.

According to a preferred aspect of the invention, different drugs are released from the matrix in a time-controlled manner. For example, bioactive components designed to minimize risks of bleeding, infection and/or apoptosis may be favourable to release during an early phase after implantation. The matrix can in this case be designed so that the release of the embedded compounds starts during or immediately after implantation. In case of drugs acting for an extended period of time it is preferred to release the drug slowly over days or weeks. To achieve a long-lasting effect a gene vector may be used instead of a drug or be included in the matrix in addition to a drug. By combining different release mechanisms it is possible to control the delay and rate of release of bioactive components embedded in the matrix of the electrode or probe. Upon introduction of the matrix into the physiological environment, the active component/s are released into the surrounding body fluid by different mechanisms such as diffusion, swelling followed by diffusion or degradation. Any or all of these mechanisms, here termed passive release mechanisms, might be used. The rate of passive emission of the active ingredient is dependent on the structure of the matrix and its response to physiological parameters such as temperature, pH, ionic strength, enzyme concentrations. Drugs to be released with a delay may be included in separate compartments in the form of for example, microcapsules or rods inserted in parallel with the electrode, electrode bundle or array. The microspheres and microrods or microbars may comprise a material that dissolves slower than the matrix. It is also possible, although not preferred, to use materials that do not dissolve after implantation and thus, after the release of the drugs through for example pores, remains in the tissue.

The drug of the invention may also be embedded in a separate matrix biocompatible material for coating an electrode body. The arrangement of several layers of matrix material on an electrode body, each layer containing a different drug or a different combination of drugs is also within the ambit of the invention. Thereby drugs comprised by an outer matrix layer can be released before a drug comprised by an inner matrix layer. In certain applications it is necessary to provide sustained release of a drug over one month and even over several months. A slow and/or delayed release may be particularly suitable for release of substances promoting trophical tissue stimulation for enhanced tissue-electrode interaction and healing. In such case, the innermost portion of the matrix material should preferably be of low solubility in body fluids but be biodegradable. Degradation of the coating material can be for making a drug slowly accessible. A slowly dissolving or degrading matrix material will gradually release a drug. For slow release a drug may be chemically linked to the matrix material or sterically blocked from diffusion through a swollen matrix. The drug of the invention may also be part of a polymer matrix material, becoming accessible as a bioactive monomer upon degradation of the polymer.

According to another preferred aspect of the invention the electrode matrix or array matrix is covered with a thin coating containing a drug, such as a drug counteracting possible acute detrimental effects due to the insertion procedure, such as bleedings or microbial contaminations, the coating being released within a short time after insertion of the electrodes into the tissue.

In a further embodiment of the invention, charged bioactive components can be made accessible by active release, for example by applying a voltage between the inner core of an electrode and another electrode and/or the surrounding tissue. This will lead to electrophoresis of charged components contained in the coating of the electrode. This can also be combined with charged layers to facilitate gradual migration if desired (U.S. Pat. No. 6,316,018). Alternatively, the release can be controlled by the use of externally applied stimuli such as ultrasound or electrical/magnetic fields. Uncharged bioactive components can also be encapsulated in dissolvable charged microcapsules that can be caused to migrate to the surface of the coating by application of a voltage.

For a drug designed to be released during heating or burning of tissue (e.g. for ablation of tissue, tumors, ligation of vessels etc.) a significantly higher temperature threshold can be used (as compared to release at body-temperature). Increase of temperature will change physical properties of the coating thus allowing the diffusion of the bioactive component into the neighbouring tissue. Example of a material having a such property is poly(N-isopropylacrylamide-co-acrylamide) co-polymer. The ratio between N-isopropylacrylamide and acrylamide will determine the temperature threshold. (Fundueanu, Acta Biomaterialia, Volume 5, Issue 1, January 2009, Pages 363-373).

Time-controlled release of bioactive components may also be controlled by specific cleavage or enzymatic degradation of certain parts of the matrix. This can be obtained by adding thin enzymatically degradable layers encapsulating the bioactive components (Itoh et al. 2008) or by conjugating the bioactive components to other molecules requiring cleavage for release. In one embodiment of this design the bioactive molecules are part of the matrix polymer itself, thus being released by biologically controlled cleavage/ degradation of the matrix.

Alternatively/additionally, an agent embedded in the matrix may not be initially bioactive but can become so through a process of activation, such as by hydrolytic cleavage or enzymatic degradation. By this a drug may be made selectively accessible in different cell- or tissue types and in a differential time-controlled manner. For long-term therapeutic effect gene transfer is believed to be more efficient than pharmacological treatment, and may thus be the treatment of choice for anti-inflammatory/anti-scaring conditioning of tissue surrounding an implant. In addition to minimizing inflammatory tissue response, gene therapy offers also a possibility of experimentally altering properties of surrounding neurons, thereby enabling experimental manipulation on a molecular level. Inducing changes in gene expression offers further interesting experimental applications when combined with electrophysiological stimulation paradigms utilizing the implanted electrodes.

In a case where it is desirable to administrate the drugs in precise amounts over extended periods of time, catheters attached to a drug delivery system may, in addition, be used for drug delivery in the tissue receiving the implant. In this case the catheters are preferably embedded in the matrix. The catheters can have one or several hole through which the drug solution can pass into the tissue. Several drug delivery system operating either as implantable minipumps (intrathecal pumps: U.S. Pat. Nos. 5,820,589, 6,375,655. 7,229,477; CNS pump: U.S. Pat. No. 7,351,239; osmotic pumps: U.S. Pat. Nos. 6,471,688, 6,632,217) or as external pumps (percutaneous pumps: U.S. Pat. Nos. 7,471,689, 6,632,217) are known in the art. The catheters can either be made of slowly dissolvable material or non-dissolvable material. It is also within the ambit of the invention to combine electrodes and microdialysis or electrodes and voltammetry to measure released bioactive molecules in the tissue as a consequence of electrical stimulation or natural tissue activity. i.e. neurotransmitters such as small molecule neurotransmitters (for example acetylcholine, dopamine, serotonin, histamin, norepinephrine and epinephrine), amino acids (for example GABA, glycine and glutamate), neuroactive peptides (for example bradykinin, substance P, neurotensin, endorphins, enkephalin, dynorphins, neuropeptide Y, somatostatin, cholecystokinin) and soluble gases (for example nitric oxide).

Also preferred is a drug that stops minor bleedings induced by the electrode insertion procedure, for instance a coagulation factor. Most preferred is factor VIII or a functional derivative thereof. Other preferred coagulation stimulating drugs comprise combinations of factor IX, II, VII and X; factor IX; a combination of von Willebrand factor and factor VIII; factor VIIa or human fibrinogen.

Also preferred is a drug controlling vasoconstriction, such as a drug promoting the production of NO, in particular glyceryl nitrate or a functional derivative thereof. In cases where there is a risk that local vasoconstriction may lead to a brain infarct due to clogging of the affected vessel a drug against trombocyte aggregation can be used, such as, for instance, klopidogrel, tiklopidine, acetylsalicylic acid, dipyramidol, iloprost, abciximab, eptifibatid, tirofiban. Local vasoconstriction may also be treated by a drug for inducing peripheral vasodilatation such as ergoloid mesylate.

For preventing or combating local infection a drug comprised by the electrode or array matrix is selected from the group of antibiotics. In selecting a proper antibiotic, the kind of bacterial strain to be fought and its resistance pattern must be taken into account. Examples of useful antibiotics are doxycyklin; lymecyklin; oxitetracyklin, tetracyklin; tigecyklin; kloramfenikol; ampicillin; amoxycyklin; pivmecillinam; mecillinam; bensylpenicillin; fenoximetylpenicillin; dicloxacillin; kloxacillin; flukloxacillin; amoxicillin combined with enzyme blockers; piperacillin combined with ensyme blockers; cefalexin; cefadroxil; cefuroxim; lorakarbef; cefotaxim; ceftazidim; ceftriaxon; ceftibuten; cefepim; aztreonam; meropenem; artapenem; imipenem combined with enzyme blockers; trimetoprim; sulfametoxazol and trimetoprim; erytromycin; roxitromycin; klaritromycin; azitromycin; telitromycin; klindamycin; tobramycin; gentamycin; amikacin; netilmycin; ofloxacin; ciprofloxacin; norfloxacin; levofloxacin; moxifloxacin; vankomycin; teikoplanin; fusidic acid; metronidazol; tinidazol; nitrofurantoin; metenamin; linezolid; daptomycin.

Drugs according to the invention for controlling astrocytic and microglial responses comprise naturally occurring agents selected from interleukins, neurokinins, transforming growth factors, epidermal growth factors, oestrogen, neuropeptides, cannabinoids and neurotrophic factors, and their combinations. Artificially derived agents may also be used, for instance minocycline. Interleukin and growth factor antagonists are also included to the extent that the are capable of controlling glial response after insertion of an electrode, an bundle of electrodes or an array of bundles of electrodes of the invention into central nervous system tissue.

Further drugs according to the invention comprise NSAIDs, glucocorticoids, prostaglandins, and agents promoting cell adhesion. Furthermore, anti-inflammatory and immunosuppressant drugs are included, which can be used to control glial response, such as natural or synthetic glucocorticoids, for instance dexamethasone, and certain NSAIDs such as indomethacin.

Drugs promoting the survival of neurons, such as neurotrophins and their combinations are also comprised by the invention. Neurotrophins of particular interest include nerve growth factor, brain-derived neurotrophic factor, basic fibroblast growth factor, glial-derived neurotrophic factor, neurotrophin-3, neurotrophin-4/5, neurotrophin 6, insulin-like growth factor, epidermal growth factor, and neurturin. Also included are lazaroids, superoxide dismutase, caspase inhibitors, inhibitor of apoptosis proteins (IAPs), Bcl-2 (B-cell lymphoma 2) family members and flunarizine, which may promote cell survival or inhibit cell death, apoptosis and/or necrosis of neurons after trauma or ischemia. Furthermore, tetracycline can be used as a drug with both neuroprotective action and anti-inflammatory effect. Further useful agent include ECM proteins (extra cellular matrix proteins, mainly proteoglycans), tenascins, hyaluronic acid and laminin, which can promote neurotrophic support and survival (cf. U.S. Patent Application No. 2007/0198063 and U.S. Pat. No. 5,202,120, which are incorporated herein by reference).

The drug of the invention furthermore include agents preventing the formation of connective tissue and promoting angiogenesis, for instance vasoactive intestinal peptide (VIP) and vascular endothelial growth factor (VEGF).

In another embodiment of the invention, cells in tissue surrounding an electrode, a bundle of electrodes or an array of electrode bundles of the invention are manipulated through the delivery of genetic vectors giving rise to modification of gene expression and translation of certain proteins (Lowenstein et al., 2007; Storek et al, 2008) The genetic material is preferably delivered to the surrounding cells by means of a viral vector embedded in the coating material or encapsulated in microspheres disposed therein. Adenoassociated viral vector systems are known in the art, which, upon injection into the brain, will lead to expression of the inserted gene in neighbouring neurons for at least 10 months (U.S. Pat. No. 6,436,708 incorporated herein by reference). Other viral vector systems such as Herpes simples virus (HSV), adenovirus or lentivirus based systems known to be efficient in regards of topical gene delivery into neurons and/or glial cells are also within the ambit of the present invention. Although not particularly preferred, a retroviral vector may optionally be produced by other cells immobilized in the matrix (cf U.S. Pat. No. 6,027,721).

For certain applications non-viral vector systems are preferred means for gene delivery. Such systems include, for instance, plasmid liposome complexes or cationic lipid systems. To facilitate transport of plasmids into surrounding cells using non-viral transfection systems, pulses of electrical current may be passes through an electrode of the invention to effect electroporation of plasma membranes, resulting in a localized and controlled gene transfection (Jaroszeski et al., 1999).

While the drug types mentioned above serve to reduce adverse reactions and complications caused by soft tissue reacting against foreign implants, drugs with other properties may also be comprised by the matrix and/or the coating of individual electrode. In one embodiment of the invention, a bioactive molecule considered to be a drug candidate is embedded in the matrix or the coating of a recording electrode. Embedding different bioactive molecules of this kind in the coatings of the electrodes of an electrode bundle allows to record electrical signals from different neurons and thus the simultaneous screening of multiple drug candidates.

In another embodiment of the invention, markers used to stain or identify neurons from which recordings are made are embedded in the coating of the different electrodes. Such markers include fluorophores, including voltage and calcium sensitive molecules (for example Fluo3 that can be used to measure calcium concentration) that are taken up by neurons or glia close to the electrode tips. Fluorophores that are not easily released from the electrodes may be used for identification of the electrodes. Fluorophores may not only serve as a neuronal stain but may also be used to measure e.g. the intracellular calcium concentration in cells or measure the potential of the neuronal membrane. Using a combination of confocal microscopy or 2-photon microscopy with recording/stimulation through the individual electrodes of the invention and/or optical stimulation through embedded optical fibers it is then possible to identify which of the neurons are recorded/stimulated by which electrode in the multichannel electrode.

In one preferred embodiment of the invention the drug for incorporation into a matrix of the invention is encapsulated in a microsphere. Such a microsphere can range in size from a few nanometers to a tenth of a millimetre. For instance, the following microencapsulation technologies can be used for encapsulating the drug of the invention: spray drying, spray chilling, rotary disk atomization, fluid bed coating, stationary nozzle coextrusion, centrifugal head co-extrusion, submerged nozzle co-extrusion, pan coating, phase separation, solvent evaporation, solvent extraction, interfacial polymerization, simple or complex co-acervation, in-situ polymerization, liposome technology, nanoencapsulation. For instance, the following materials can be used as the shell building material of a microcapsule: proteins, polysaccharides, starches, waxes, fats and other natural and synthetic polymers. An optimal release rate of the encapsulated drug can be achieved by proper selection of the material used to construct the spheres, the size of the spheres, type and amount of embedded drug and additives incorporated in the spheres. Release rates of microspheres are commonly of first order. However, zero order release rates can be achieved by using different methods such as providing an optimal ratio of different sized particles and depot layer techniques. The microspheres of the invention might themselves contain smaller spheres in which the drug is embedded. Microspheres can be designed to be dissolvable but at a slower rate than the surrounding matrix. Alternatively the microspheres can be designed to be non-dissolvable. For example, biocompatible synthetic polymers such as polyurethane (including polycarbonate urethanes), isobutylene, polystyrene-isobutylene-polystyrene, silicone (e.g., polysiloxane and substituted polysiloxane), a thermoplastic elastomer, an ethylene vinyl acetate copolymer, a polyolefin elastomer, ethylene propylene diene M-class rubber, polyamide elastomer, hydrogel or combinations thereof can be used for this purpose. Such hydrogel polymers include, but are not limited to, derivatives of 2-hydroxyethylmethacrylate, polyvinyl alcohol, polyethylene oxide, polyethylene glycol, polyurethane hydrogel, naturally occurring hydrogels, e.g., gelatin, hyaluronic acid, cross-linked albumin, etc. or combinations thereof.

Method of Manufacture

According to the invention is also disclosed a method of manufacture of an electrode body of the invention embedded in a matrix. The method comprises providing a fixation means, fixing the electrode body and, optionally additional elements to be imbedded, such as optical fibres, contractile elements, etc., in the fixation means in a desired configuration, applying a sheath covering the thus fixed electrode body and accessories except for at the proximal coupling section thereof, applying a solution or suspension of a first matrix material on the electrode in a manner so as to cover the portions of the electrode intended to be embedded, allowing the solvent/dispersant of the matrix solution or suspension, respectively, to evaporate or harden, removing the sheath, and releasing the electrode from the fixation means. For embedment of the electrode in two matrix materials so as to form corresponding matrix compartments, each enclosing a portion of the electrode, an appropriate portion of the electrode body fixed by a fixation means as described above is coated with a solution or suspension of the first matrix material, the solvent/dispersant of which is subsequently evaporated, followed by coating the portion of the electrode body remaining to be coated with a solution or suspension of the second matrix material, subsequently evaporating the solvent/dispersant of the second matrix material, and releasing the electrode from the fixation means. In the method the electrode body is preferably disposed in a sheath of smooth material of low wettability such as a polyfluorinated hydrocarbon polymer or silicon rubber, and fixed therein. To facilitate solvent evaporation the sheath material is advantageously porous, in particular micro-porous. After application and drying of the matrix material(s), the electrode is withdrawn from the sheath.

An alternative method of embedding an electrode body of the invention into two matrix materials forming distinct matrix compartments, comprises embedding the entire electrode body in a first matrix material, dissolving a portion of the first matrix material, preferably a distal portion extending from the distal end, covering the now non-embedded distal portion of the electrode body with a second matrix material by, for instance, taking recourse to a sheath applied on the non-embedded distal portion, filling the sheath with a solution or suspension of the second matrix material, evaporating the solvent so as to dry/harden the second matrix material, and removing the sheath.

The electrode body of the invention can be coated by using a single coating technique or combination of coating techniques, such as by dip coating, spray coating, melting processes including extrusion, compression molding and injection molding or a combination of different techniques.

In a representative example of a stepwise procedure, the electrode body is first dip-coated with a suitable resorbable polymer or blend of polymers, in particular collagen, gelatine, polyvinyl alcohol and starch, dissolved in a proper solvent. Other polymers can also be used. The thickness of the polymer layer is controlled in manner known to a person skilled in the art. The coating is then subjected to a drying step. The dip coating and drying steps can be done once or can be repeated, depending on required thickness of the final coating. In the next step the polymer is loaded with the drug. The electrode is submerged into a solution containing the drug. The solvent used should be one in which the polymer swells and in which the drug dissolves. After an appropriate contact time, such as from less than a second to 5 min or more, the electrode is removed from the solution and the matrix dried by evaporation of the solvent, possibly under reduced pressure.

In a one-pot procedure the electrode body is submerged into a solution of the polymer and the drug of choice in an optimal concentration for a desired coat thickness and a desired drug loading. The electrode is then removed from the solution and the solvent evaporated, possibly under reduced pressure.

Alternatively the coating is generated by spray coating, in which a polymer/drug solution in a suitable solvent is sprayed on the electrode body. The thickness of the coating can be controlled by the number of spraying and drying (evaporation) cycles and the amount of polymer and drug in the solution.

Also comprised by the invention are hydrogel coats of partially hydrolyzed water-soluble polymers such as polyvinyl alcohol, polyacrylic acid and derivatives of polyacrylic acid, e.g., poly(N-isopropylacrylamide). An increase in temperature makes these hydrogels contract, thereby forcing the drug out of the coating. Alternatively, the temperature-sensitive hydrogel is an interpenetrating hydrogel network of poly(acrylamide) and poly(acrylic acid), and the increase in temperature causes the hydrogel to swell, thereby allowing the drug to diffuse out of the gel.

Also comprised by the invention is the use of a polymer or a polymer blends for electrically triggered release, such as polyvinyl alcohol/chitosan.

Method of Implantation

According to the invention is also disclosed a method of inserting or implanting an electrode, an electrode bundle and an array of electrodes or electrode bundles of the invention into soft tissue.

A method of inserting or implanting a flexible medical microelectrode of the invention in tissue in a desired configuration comprises: providing the electrode in the desired configuration at least partially embedded in a substantially rigid biocompatible water soluble or biodegradable matrix comprising a drug capable of release into a body fluid; inserting or implanting the matrix embedded electrode into tissue; allowing the matrix to dissolve or to be degraded in situ. It is preferred for the matrix to comprise a proximal section of lower dissolution or degradation rate and a distal section of higher dissolution or degradation rate.

A method of inserting or implanting a medical microelectrode bundle of the invention into tissue in a desired configuration comprises: providing the electrode bundle in the desired configuration embedded in a substantially rigid biocompatible shared electrode matrix that is soluble or biodegradable in a body fluid, the shared electrode matrix comprising a drug capable release into a body fluid; inserting or implanting the matrix embedded electrode bundle into tissue; allowing the shared electrode matrix to dissolve or be degraded in situ. It is preferred for the shared electrode matrix to comprise a proximal section of lower dissolution or degradation rate and a distal section of higher dissolution or degradation rate.

A method of inserting or implanting an array of electrode matrix embedded medical microelectrodes or microelectrode bundles of the invention embedded in a common array matrix into tissue in a desired configuration comprises: providing an array of microelectrodes or microelectrode bundles in a desired configuration embedded in a substantially rigid array matrix that is soluble or biodegradable in a body fluid, the array matrix comprising a drug capable of release into a body fluid; inserting or implanting the matrix embedded array of microelectrodes or microelectrode bundles into tissue; allowing the electrode/shared electrode matrices and the array matrix to dissolve or be degraded in situ.

Uses

The invention also relates to the use of the matrix-embedded electrode, the matrix-embedded electrode bundle or the array of matrix-embedded electrode bundles for long-lasting nerve stimulation, multi-channel recordings of electrical neuronal activity and levels of transmitter substance through measurements of redox reactions and lesions of the tissue for scientific, medical and animal care purposes.

According to a preferred aspect of the invention the microelectrode, the microelectrode bundle, and the array of microelectrodes or microelectrode bundles of the invention is used in a patient or animal for: recording signals from neurons remaining after brain and/or spinal damage; stimulating neurons to compensate for lost functions; providing pain relief by stimulation of analgesic brain stem centres; providing relief or decrease of tremor and other motor symptoms in Parkinson's disease; relief or decrease of choreatic and other involuntary movements by stimulation within the basal ganglia or associated nuclei; boosting memory by stimulation of cholinergic and/or monoaminergic nuclei in case of Alzheimer's disease or other degenerative disease; control of mood, aggression, anxiety, phobia, affect, sexual over-activity, impotence, eating disturbances by stimulation of limbic centres or other brain areas; providing rehabilitation after stroke or damage of the brain and/or spinal cord by stimulation of remaining connections in the cortex cerebri or descending motor pathways; providing re-establishment of control of spinal functions such as bladder and bowel emptying after spinal cord injury by stimulating relevant parts of the spinal cord; providing control of spasticity by stimulation of inhibitory supraspinal descending centres or appropriate cerebellar areas; providing re-establishment of somatosensory, auditory, visual, olfactory senses by stimulation of relevant nuclei in the spinal cord and the brain.

According to another preferred aspect of the invention the microelectrode, the microelectrode bundle, and the array of microelectrodes or microelectrode bundles of the invention is used in a patient or animal for combined monitoring and stimulation, in particular for: monitoring of epileptic attacks by electrodes implanted into the epileptic focus coupled to a system for delivering antiepileptic drugs or electrical pulses; compensating for a lost connection in the motor system by recording central motor commands, followed by stimulating executive parts of the motor system distal to a lesions; recordings of blood glucose levels to control the hormone release.

According to a further preferred aspect of the invention the microelectrode, the microelectrode bundle, and the array of microelectrodes or microelectrode bundles of the invention is used in a patient or animal for locally lesioning tissue, in particular tumour or abnormally active or epileptogenic nervous tissue by passing current of sufficient magnitude through said electrode, electrode bundle or array of electrode bundles.

In biomedical research, use of the microelectrode, the microelectrode bundle, and the array of microelectrodes or microelectrode bundles of the invention can be used for studying normal and pathological functions of the brain and spinal cord, in particular over a long time.

In a patient having a neuroprosthetic device, the microelectrode, the microelectrode bundle, and the array of microelectrodes or microelectrode bundles of the invention can be used to form an interface between a nerve and said device.

In a patient or an animal, the microelectrode, the microelectrode bundle, and the array of microelectrodes or microelectrode bundles of the invention can be used for controlling the function of an endocrine or exocrine organ, such as in controlling hormone secretion.

In a patient or animal, the microelectrode, the microelectrode bundle, and the array of microelectrodes or microelectrode bundles of the invention can be used for controlling the function of one or more skeletal muscles or a heart muscle.

The invention will now be explained in more detail by reference to a number of preferred embodiments illustrated in a rough drawing comprising a number of figures, which are however not to scale.

DESCRIPTION OF THE FIGURES

FIG. 1a is a longitudinal section through a first embodiment of the electrode of the invention comprising an electrode body including a tip section and a main section of a non-conductive silk core coated with silver and gold, a polymer insulating coat on the main section, the main section having a wavy configuration, the matrix not being shown;

FIGS. 1b and 1c are transverse sections A-A, B-B through the electrode body, respectively, of the electrode of FIG. 1, the matrix element not being shown;

FIG. 1d is the embodiment of FIG. 1a, in an extended state, upon dissolution of the matrix in a body fluid;

FIG. 2a is a longitudinal section through a second embodiment of the electrode of the invention, in a state corresponding to that of the embodiment of FIG. 1a, the matrix element not being shown;

FIG. 2b is an enlarged partial view of the tip of the electrode of FIG. 2a, the matrix element not being shown;

FIG. 3a is a longitudinal section through a third embodiment of the electrode of the invention, in a state corresponding to that of FIG. 1a, the matrix element not being shown;

FIG. 3b is an enlarged partial view of the tip of the electrode of FIG. 3a, the matrix element not being shown;

FIGS. 4a-4c are longitudinal sections through a fourth embodiment of the electrode of the invention embedded in a dissolvable matrix (4a), in a state after insertion into a soft tissue and after dissolution of the matrix (4b), and in an extended state (4c) in the tissue;

FIG. 5a is a longitudinal section through a first embodiment of a bundle of electrodes of the invention;

FIG. 5b is a transverse section C-C through the embodiment of FIG. 5a;

FIG. 6 is a longitudinal section through a second embodiment of a bundle of electrodes of the invention embedded in a combination of dissolvable matrices, in a view corresponding to the view of the bundle of electrodes in FIG. 5a;

FIG. 7b is a transverse section D-D through the electrode bundle array of FIG. 7a;

FIGS. 8b-8f illustrate the process of consecutive dissolution of the dissolvable matrices of the array of FIGS. 8, 8a inserted into soft tissue, in the same view as in FIG. 8;

FIG. 9 is a third embodiment of the electrode bundle array of the invention comprising an optical fibre, in a longitudinal section corresponding to that of FIG. 8;

FIGS. 10-11 illustrate a fourth and a fifth embodiment of the electrode of the invention, in views corresponding to that of FIG. 1a, the matrix element not being shown;

FIG. 12 illustrates a sixth embodiment of the electrode of the invention, in a longitudinal section G-G (FIG. 12a), in a view corresponding to that of FIG. 1a, the matrix element not being shown;

FIG. 12a is an enlarged top view, in a proximal direction, of the electrode of FIG. 12, the matrix element not being shown;

FIG. 13 is a longitudinal section through a third embodiment of a bundle of electrodes of the invention joined at their proximal ends by an electrode holder disk, in a view corresponding to the view of the bundle of electrodes in FIG. 5a;

FIG. 14 is a longitudinal section through a fourth embodiment of the electrode bundle array of the invention comprising four electrode bundles of the kind shown in FIG. 13 mounted on an array holder disk, in a view corresponding to the view of the array of bundle of electrodes of FIG. 7 but with a portion of the distal terminal section omitted;

FIGS. 16a-16b illustrate an embodiment of an electrode array of the invention mounted on a base dissolvable in an aqueous body fluid, in a view corresponding to the view of the bundle of electrodes in FIG. 5a;

FIG. 18 is an axial section through a still further embodiment of the electrode of the invention, in the same view as that of the embodiment in FIG. 17a;

DETAILED DESCRIPTION OF THE INVENTION

Figure 7B:
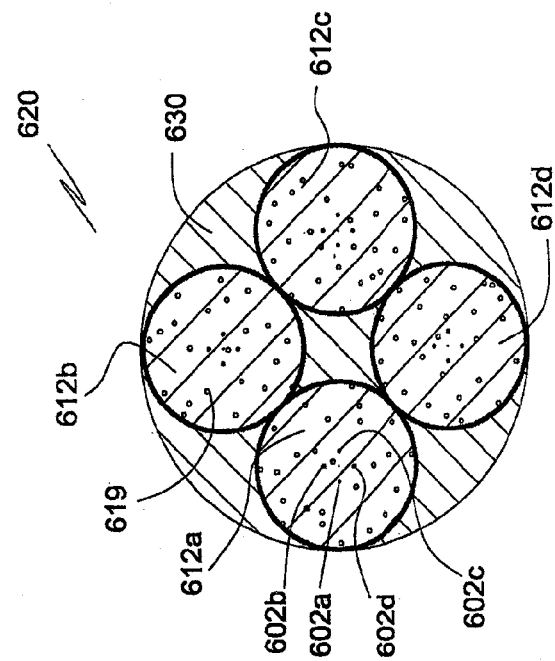

The first embodiment 1 of the electrode of the invention of FIGS. 1a-1c comprising a generally oblong electrode body (2, 3, 4) including a waveform main section 2 joined to a proximal coupling section 4 at its first, proximal end and to a tip section 3 at its second, distal end, the tip section provided with a point or tip 5, which may be sharp or blunt. A blunt tip 5 has the advantage of avoiding damaging blood vessels if disposed in a tissue rich in such vessels. The proximal coupling section 4 is a pearl of solder connecting the electrode body 2, 3, 4 at its proximal end with a thin insulated conductor for electrical connection of the electrode body 2, 3, 4 with an electrical apparatus 10. The electrical apparatus 10 may be of various kind, such as for feeding an electric current to the electrode and/or for receiving electrical signals from the electrode. The electrode body 2, 3, 4 is flexible but substantially not resilient. As shown in the enlarged transversal section of FIG. 1c it consists of a core 7, an intermediate layer 8, and a coat 9. The core 7 is a silk thread on which the thin intermediate layer 8 of chromium has been deposed by ion sputtering. The intermediate layer 8 is covered by a coat 9 of polyvinyl formal. In contrast to the main section 2 the tip section 3 is not insulated, that is, lacks the coat 9 (FIG. 1b). Applying a slight force to the opposite ends of the electrode body 2, 3, 4 so as to draw it apart results in the extended, substantially straight configuration of the electrode body shown in FIG. 1d.

The second embodiment 101 of the electrode of the invention shown in FIGS. 2a, 2b differs from the first embodiment by the waveform pattern of its body main section 102. Reference nos. 103, 104 refer to the tip section, which ends in a sharp point 105, and to the electrode proximal coupling section, respectively.

The third embodiment 201 of the electrode of the invention shown in FIGS. 3a, 3b differs from the first embodiment by a roughened surface portion 210 of the tip section 203 extending from the blunt tip 205 in the direction of the wavy electrode body main section 202 and the electrode proximal coupling section 204. The roughening improves retention at the implantation site and increases the contact area of the electrode with surrounding cells, thereby lowering the electrical resistance between the electrode and the cells.

In FIG. 4a a fourth embodiment 321 of the electrode of the invention is shown with its tip section 303 and its body main section 302 embedded in a matrix shell 312 of water soluble material in a manner so that the sharp electrode tip 305 points in the same direction as the blunt matrix shell tip 313. At a distance from the tip 305 a barb 314 extends in a skew proximal direction from the tip section 303. Except for at its conductor lead 306 bearing proximal coupling section 304 the electrode main and tip sections 202, 203 are fully embedded in the matrix shell 312. The embedded electrode body main section 302 has a zigzag configuration. The combination 321 of electrode tip 303 and main 301 sections, at the one hand, and the matrix shell 312, on the other, is a conformationally stabilized electrode. In this stabilized form 321 the electrode can be inserted into soft tissue while retaining the zigzag configuration of its body main section 203. Within a short time upon insertion the matrix shell 312 is dissolved by body fluid (FIG. 4b); the electrode main section does 203 substantially retain the zigzag configuration in which it had been embedded in the matrix shell 312 and in which it had been inserted into the tissue. By the barb 314 the combination 301 including electrode tip and main sections 202, 203 is anchored in the tissue, in particular against a force seeking to withdraw it. By application of a withdrawing force to the proximal coupling section 304 the electrode body main section 302 is straightened, viz. extended, so as to assume the straightened configuration 302' shown in FIG. 4c. In an exemplary embodiment of the invention, the matrix shell 312 is sodium hyaluronate comprising the serotonin antagonist (5-HT$_3$ antagonist) ondansetron (12% by weight) dispersed therein.

A first embodiment of a matrix-embedded bundle 411 of four electrode bodies of the invention is shown in FIGS. 5a, 5b. The electrode bodies 402a, 403a; 402x, 403c, which are of same kind as that 101 of FIGS. 2a, 2b, are disposed in parallel and equidistantly from the rotational axis S of the bundle 411 in a dissolvable matrix body 412 of sodium hyaluronate comprising a 0.05% (w/w) solid solution of ondansetron, a serotonin (5-HT$_3$) antagonist. In respect of the electrode body 402a of the first electrode, the bodies 402b, 402c, 402d of the other electrodes are disposed in an angle of 90°, 180° and 240°, respectively. In FIG. 5a the tip sections 403a, 403c and the proximal coupling sections 404a, 404c of the first and third electrodes, respectively, are also shown. The generally cylindrically tapering matrix body 412 tapers in a distal direction, only slightly at start but more pronounced towards its distal pointed end 413.

The second embodiment of a matrix-embedded electrode bundle 511 of four electrode bodies of the invention shown in FIG. 6 comprises four electrode bodies 502a, 502b of the kind disclosed in FIGS. 2a, 2b and in the same disposition in respect of a rotational axis S' as in the matrix-embedded electrode bundle 411 of FIGS. 5a, 5b. In contrast to the embodiment of FIGS. 5a, 5b the matrix body comprises two sections, a proximal section 512' enclosing the electrode bodies' main sections 502a, 502c, etc., and a distal section 512" enclosing the tip sections 503a, 503c. The dissolution rate of the proximal matrix body section 512' is slower than that of the distal matrix body section 512". This allows, for instance, insertion of the entire matrix-embedded bundle 511 to a desired first depth or level of a soft tissue and, upon dissolution of the distal section 512" further insertion of the bundle 511 having lost its distal section 512" to a second depth or level, during which the no longer matrix embedded tip sections 503a, 503c may bend, for instance bend away from the central axis S'. In an exemplary embodiment of the invention, the proximal matrix body section 512' consists of gelatine/lactose (9:1, w/w), whereas the distal body section 512" consists of mannose comprising 5% by weight of gelatin and 0.01% by weight of factor VIII.

Figure 7A:
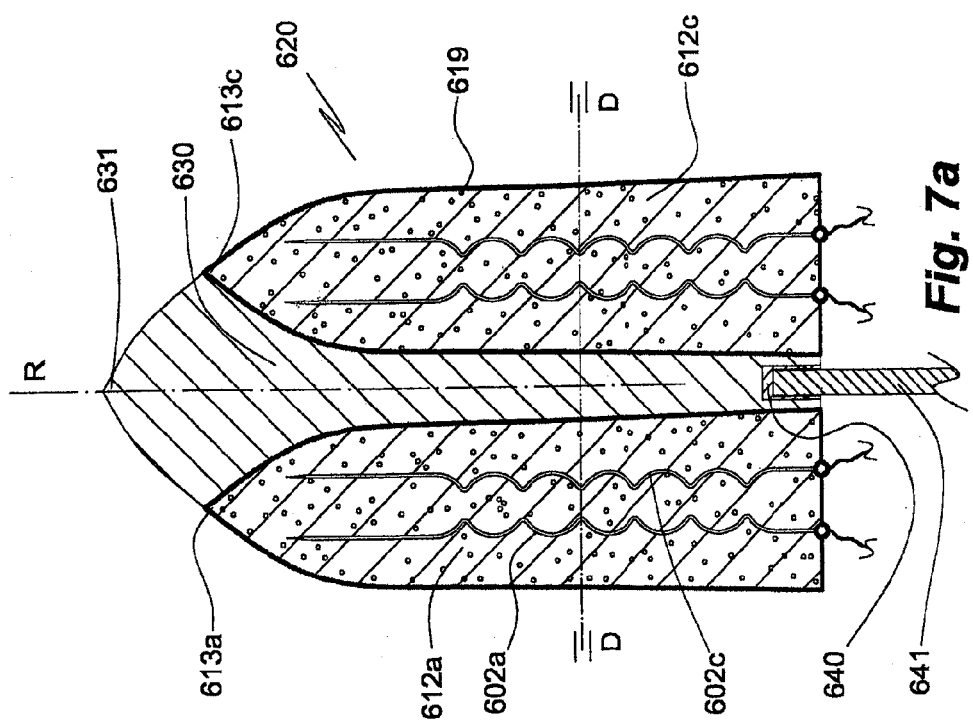
FIG. 7a is a longitudinal section through a first embodiment of the electrode bundle array of the invention comprising four electrode bundles of the embodiment of FIGS. 5a, 5b.

A distally pointed 631 array 620 of electrode bundles of the invention comprises four matrix-embedded electrode bundles disposed equidistantly and rotationally symmetrically (four-fold rotational symmetry) from an array axis R of the invention (FIGS. 7a, 7b). The array 620 comprises four electrode bundles of the kind illustrated in FIGS. 5a, 5b, of which only the main body sections 602a-602d of the first bundle are identified by reference numbers. The electrode bundles are embedded in solid dissolvable electrode matrices 612a-612d of same kind, respectively, comprising polyglycolic acid microspheres 619 containing 10% by weight of metoprolol succinate dispersed therein. The four matrix-embedded electrode bundles are disposed in parallel with their matrix tips 613a, 613c pointing in the same, distal direction. The matrix-embedded electrode bundles are joined by an array matrix 630 of a 2:1 (w/w) mixture of galactose and agarose, which is dissolvable in an aqueous environment. The array matrix 630 is preferably different in composition and dissolution or swelling rate from the material of the electrode matrices 612a-612d. The material of the embedding matrices, that is, electrode and array matrices, may be one and the same but it is also conceivable to use material(s) with different dissolution or swelling rates for one or more of them. The array 620 is provided with a female coupling member 640 disposed centrally in the array matrix 630 at its proximal flat end face. The coupling member 640 is designed to releasingly receive a manipulation rod 641 for insertion of the array 620 into tissue.

Figures 8, 8A:
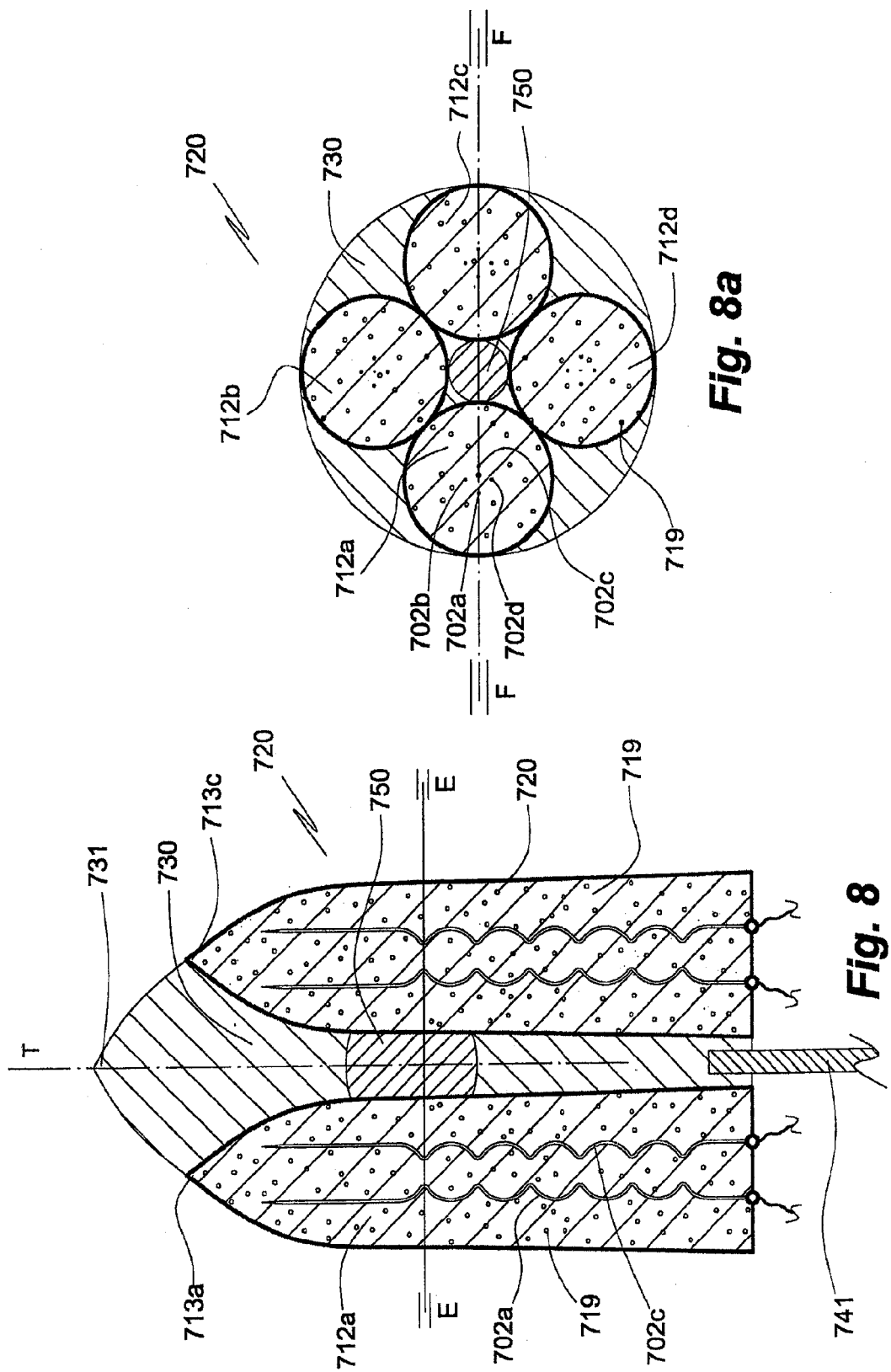
FIG. 8 is a longitudinal section F-F (FIG. 8a) through a second embodiment of the electrode bundle array of the invention embedded in a combination of dissolvable matrices and comprising a swelling means.
FIG. 8a is a transverse section E-E (FIG. 8) through the electrode bundle array of FIG. 8.

Another projectile formed pointed 731 electrode bundle array 720 of the invention of same symmetry as the array of FIGS. 7a, 7b is shown in FIGS. 8, 8a. In addition to the water soluble array matrix 730 connecting the electrode bundles of the array 720, the array comprises a swelling plug 750 disposed centrally in respect of the array axis T and extending from there in a radial direction to the innermost wall sections of the matrix bodies 712a-d of polyvinylpyrrolidone comprising 2% by weight of bromperidol in d,l-polylactic acid microspheres 719 (EP 669 128 B1), each matrix body 712a-d further comprising a matrix-embedded electrode bundle with four electrodes each, each electrode having an extendable electrode body 702a-d, etc., whereas, in an axial direction the proximal and distal faces of the plug 750 abut the array matrix or glue 730 by which the four matrix-embedded electrode bundles are kept in place. An insertion rod 741 is embedded in the central proximal portion of the array matrix 730. FIGS. 8b-8f illustrate the fate of the array 720 after insertion into soft tissue 760. FIG. 8b shows the situation immediately upon insertion of the array 720 into the tissue 760. The array 720 is still intact. FIG. 8b shows the situation about 2 minutes upon insertion during which period the matrix array 730 has dissolved in the aqueous environment of the tissue 760. Reference number 760 represents both soft tissue and fluid formed by dissolution of the glue 730. The matrix bodies 712a-d are now separated, except for a possible adhesion to the swelling plug 750 of agarose. Next the swelling plug 750, now in contact with tissue fluid, begins to swell. The situation after considerable swelling of the plug 750 is shown in FIG. 8d. The swelling plug 750 is of a material that first swells and later dissolves in contact with aqueous body fluids. It is, for instance, made of agarose or gelatin. The swelling of the plug makes the matrix-embedded electrode bundles move radially apart, the result of which is shown in FIG. 8e. Finally, the matrix bodies 712a-712d are slowly dissolving in body fluid, which results in the main body sections 702a, 702c of the electrode bodies of the first electrode bundle, the main body sections 702a", 702c" of the electrode bodies of the third electrode bundle, and the main body sections of the electrode bodies of the other electrode bundles becoming disposed in the tissue, as shown in FIG. 8f. Contact with body fluid makes the microspheres 719 leak an aqueous solution of bromperidol intended to affect neurons (not shown) in proximity of the electrodes. By incorporating a different number of microspheres 719 in each matrix 712 a-d, the amount of aqueous bromperidol leaked from microspheres 719 pertaining the respective matrix body, thus to the respective electrode bundle, can be controlled. This can be used for studying the effect of varying concentrations of a substance on neurons in a single experiment. To obtain an essentially similar effect, one could incorporate microsphere batches of same weight but differing in their content of bromoperidol into each of the matrices 721 a-d. Alternatively, one could incorporate into each of the matrix bodies 712 a-d a different drug comprised by the same kind and amount of microspheres; this would allow the comparison of the effect of different drugs on neurons in a single experiment.

The third embodiment of the electrode bundle of the invention shown in FIG. 13 comprises four longitudinally extendible electrode main body sections 802a, 802c attached to proximal coupling sections 804a, 804c. The bundle is embedded in a dissolvable matrix 812 narrowing towards its distal tip 813. The proximal coupling sections 804a, 804c are moulded in an electrode holder disk 807 from which their rear portions provided with conductors 806a, 806c extend. The electrode holder disk 807 is made of a non-conducting polymer material. This embodiment allows to keep the proximal portions of the electrode main body sections at a desired distance from each other, whereas their distal portions can move more freely in respect of each other. The matrix body 812 of agarose comprises 10% by weight of particulate levodopa 819 dispersed therein.

A third embodiment of the electrode bundle array of the invention is shown in FIG. 9. The electrode bundle array 920 comprises four matrix-embedded electrode bundles of which only two are shown. It differs from the electrode bundle array 620 of FIGS. 7a, 7b in that electrodes of the invention with tip sections 903a, 903c of varying length and electrode body main sections 902a, 902c of same length are comprised by a first electrode bundle embedded in a first electrode bundle matrix body 912a, whereas a third electrode bundle embedded in a third electrode bundle matrix body 912c comprises an electrode of the invention comprising an electrode main body section 902c" and an optical fibre 970 disposed in parallel with the electrode. The agarose electrode matrix bodies 912a, 912c comprise sustained-release poly(lactide-co-glycolide) microcapsules 919 containing about 2% by weight of leuprolide (U.S. Pat. No. 4,954,298). The electrode body main sections 902a, 902c, 902c" of the array are connected via thin flexible conductors 906a, 906c, 906c" to a control unit 960 by which they may be powered or to which they may transmit electrical nerve signals. The optical fibre 970 is shown connected to the central unit which may comprise a light source for sending radiation through the fibre into the tissue in which the fibre 970 is implanted or which may comprise means for detecting radiation emanating from the tissue received via the fibre 970.

FIGS. 10-12 illustrate further preferred embodiments of the electrode body of the invention with modified tip sections.

The electrode body 1001 of FIG. 10 comprises an extendable oblong electrode body main section 1002 and a tip section 1003 from which short tags 1011-1011''' extend radially/distally and spaced along the tip section 1003.

The electrode body 1101 of FIG. 11 comprises an extendable oblong electrode body main section 1102 and a tip section 1103 from which doubly curved tags 1111-1111'''' extend about radially and spaced along the tip section 1103.

The electrode 1201 body of FIGS. 12, 12a comprises an non-extendable straight electrode body main section 1202 and a tip section 1203 from a radial plane of which twenty-four rearwards curved tags, of which only the first and the twelfth tag 1211-01, 1211-13 extend in an umbrella-like configuration.

The electrode bundle array 1320 of the invention of FIG. 14 comprises four electrode bundles of the kind shown in FIG. 13. In the sectional view of FIG. 14 only two of them can be seen. Except for matrix bodies 1312a, 1312c and electrode holder disks 1307, 1307" only the elements of the first bundle, which comprises four electrode bodies, are provided with reference numbers. Only two of the electrodes of the first bundle are visible in the figure, the first electrode comprising an electrode body main section 1302a and the third electrode comprising an electrode body main section 1302c. The electrode bodies are embedded in a dissolvable, substantially conical array matrix 1312a that narrows towards its distal tip. Their electrode proximal coupling sections 1304a, 1304c are moulded in an electrode holder disk 1307 of a non-conducting polymer material. The holder disks 1307, 1307" are adhesively mounted (not shown) on an array holder disk 1335 with their proximal faces abutting the distal face of the array holder disk 1335. To allow the leads 1306a, 1306c of the electrodes to pass through the array holder disk 1335 the latter is provided with through bores 1337a, 1337c facing the electrode proximal coupling sections 1304a, 1304c. The electrode bundles are disposed symmetrically in respect to and equidistantly from the array long axis (not shown). Their spacing allows a central cylindrical portion 1336 extending in a distal direction from the distal face of the array holder disk 1335 to be disposed between them. A central bore in the proximal face of the cylindrical portion 1336 is arranged for releaseably holding a manipulation rod 1341 by which the array 1320 can be inserted into soft tissue. The remaining interstice between the electrode bundles is filled with a biocompatible matrix glue 1330 that is soluble in an aqueous environment. The matrix bodies 1312a, 1312c are of xanthane gum containing 8% by weight of Eudragit 100/insulin microspheres (Jain D et al., Eudragit S100 entrapped insulin microspheres for oral delivery. AAPS Pharm Sci Tech 6 (2005) E100-E107).

Figure 15A:
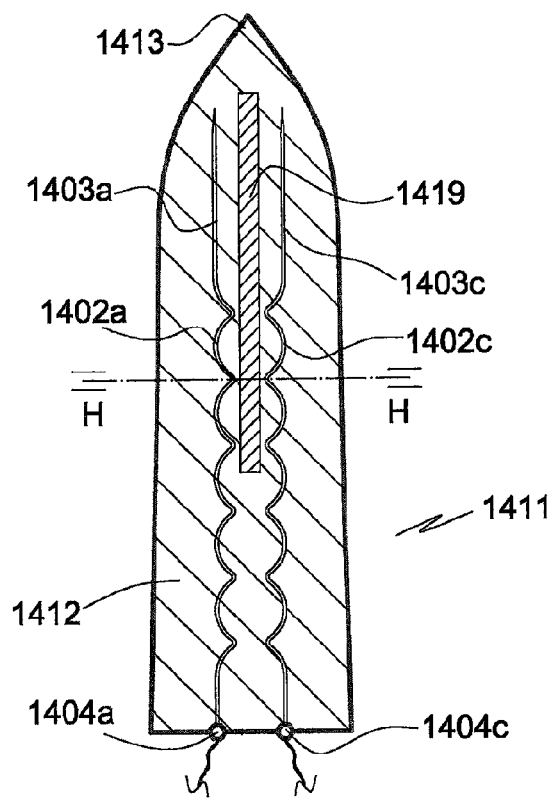
FIGS. 15a-15b illustrates a fourth embodiment of a bundle of electrodes of the invention comprising a biodegradable sustained drug release rod, in views corresponding to the views of the bundle of electrodes in FIGS. 5a, 5b (transverse section H-H)
Figure 15B:
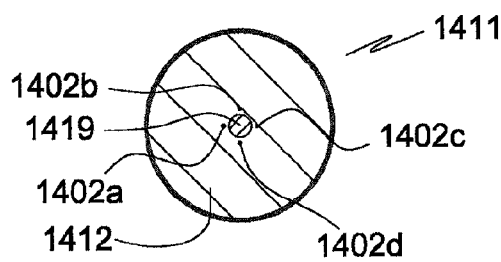

The fourth embodiment 1411 of the electrode bundle of the invention shown in FIGS. 15a, 15b comprises four electrodes bodies 1402a, 1403a; 1402c, 1403c attached to proximal coupling sections 1404a, 1404c. The electrode bodies are embedded in a dissolvable matrix body 1412 narrowing towards its distal tip 1413. Centrally in the matrix body 1412 of alginate is disposed a rod 1419 of carrageenan comprising 5% by weight of fentanyl citrate extending in an axial direction somewhat further than the electrode tips 1403a, 1403c. The electrode proximal coupling sections 1404a, 1404c are moulded in an electrode holder disk from which their rear portions provided with conductors extend. Upon dissolution of the matrix body 1412 the rod 1419 is contacted by body fluid, resulting in the electrode tip region being immersed in a fenantyl solution.

The array 1511 of four electrodes of the invention shown in FIGS. 16a-16b comprises a proximal flat base 1507, which is dissolvable in an aqueous body fluid. Four electrodes (electrode bodies 1502a-d; electrode matrix bodies 1512a-d) are mounted at the base 1507. Proximal coupling sections 1502a-d penetrate the base 1507 to allow their electrical connection at the rear (proximal) face via flexible conductors to a control unit (not shown), whereas the four electrode matrix bodies extend in a distal direction from the distal face of the base 1507, and are enclosed in array matrix element 1530, which is dissolvable in a body fluid. Particulate ciclosporin 1519 (0.1 mg per electrode, 2-5 µm (95%)) is evenly distributed in each of the electrode matrices 1512a-d of carboxymethyl cellulose (MW 20,000-40,000)/albumin 9:1 (w/w).

Figures 17A, 17B, 17C:
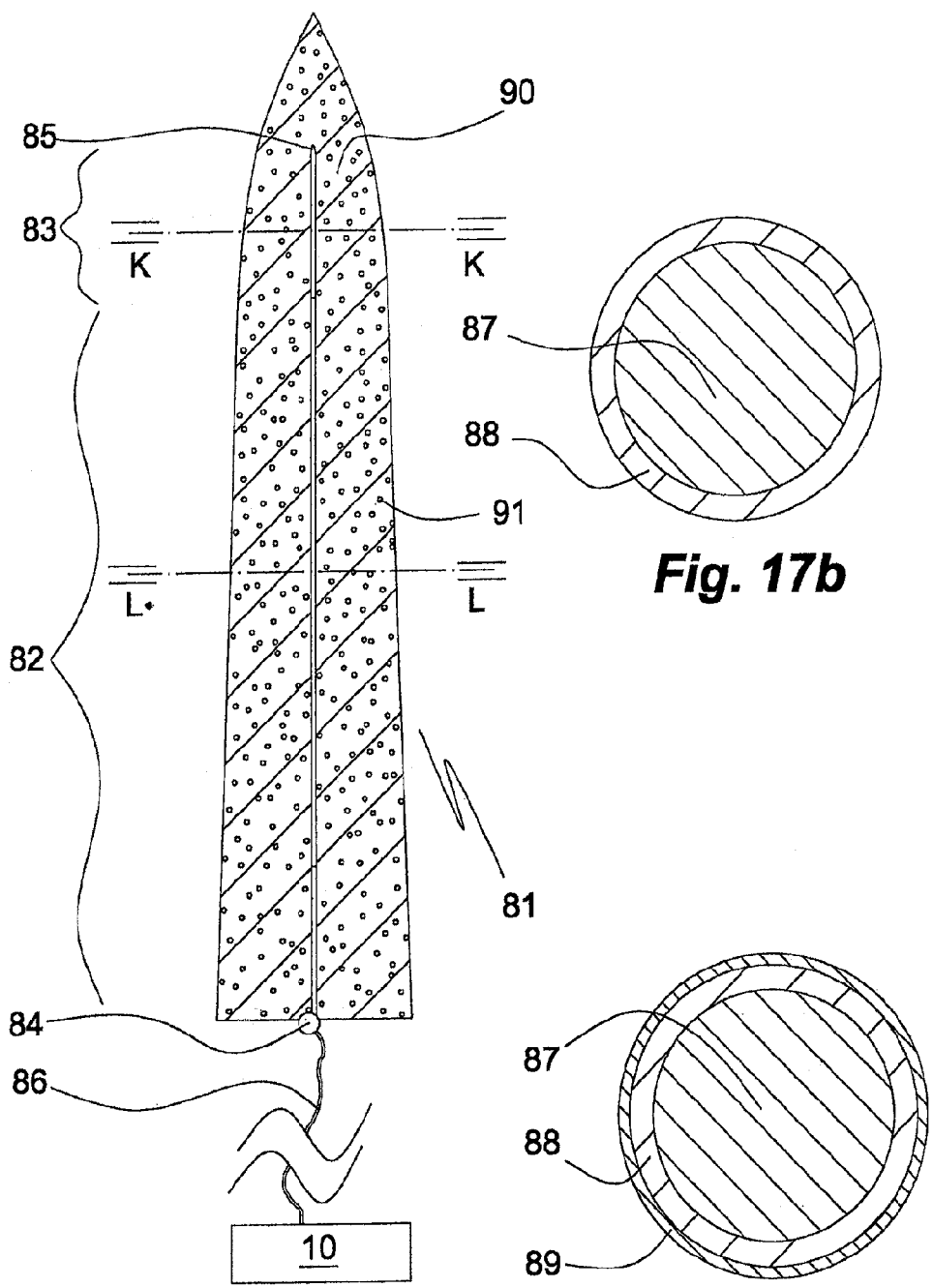
FIGS. 17a-17c illustrate a further embodiment of the electrode of the invention in an axial section and in two transverse (K-K, L-L) sections.

A further embodiment 81 of the electrode of the invention is shown in FIGS. 17a-c. Over most of its length the straight, non-extendable electrode body 82 of copper 87 covered by a thin coat 88 of gold is insulated by a lacquer 89. Only a distal terminal portion 83 including a sharp electrode tip 85 is not insulated. At a solder point 84 disposed at its proximal end the electrode body 83 is connected to a control unit 10 via a thin flexible copper wire 86. The electrode body 83 is enclosed, except at the solder point 84, by a glucose/sodium hyaluronate gelatin matrix element 90 (95:5, w/w) in which particulate nifedipine (0.05 mg per electrode, 5-10 µm (90%)) is evenly distributed.

Figure 18A:
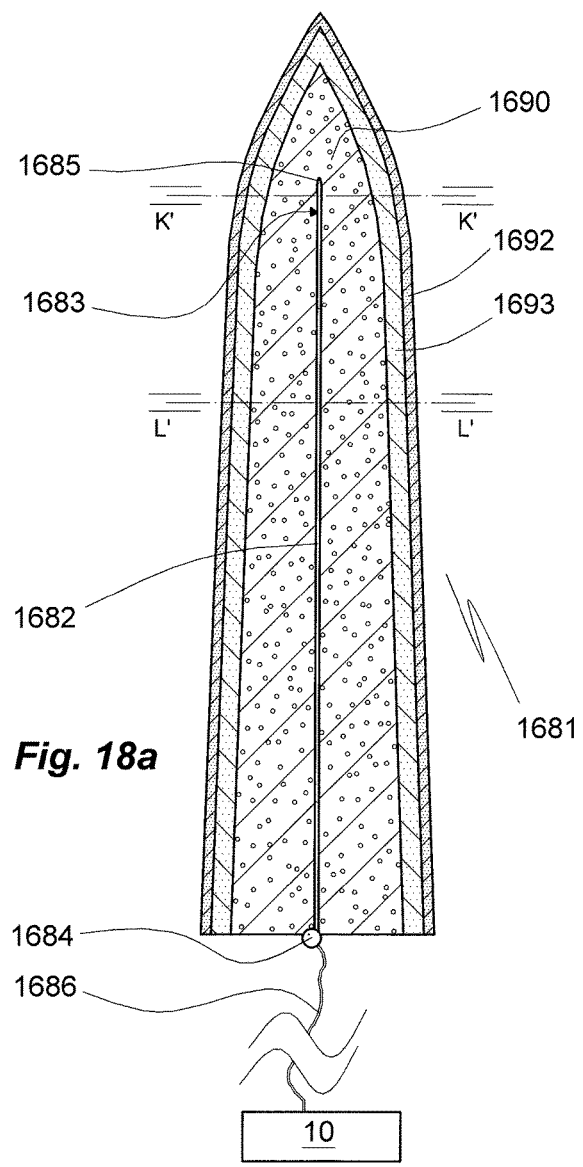
Figure 18B:
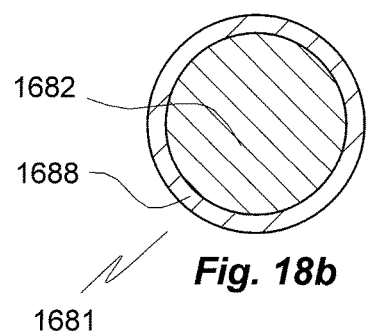
Figure 18C:
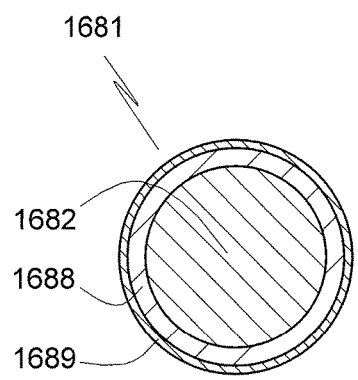

A still further embodiment 1681 of the electrode of the invention is shown in FIG. 18. Over most of its length the straight, non-extendable core body 1682 is covered by a thin coat 1688 of platinum, as illustrated in FIG. 18b and 18c, is insulated by a thin coat of polyamide 1689, as illustrated in FIG. 18c; except for other materials being used the design of the core body 1682 corresponds to that of FIGS. 17a-17c. Again, only a distal terminal portion 1683 including a sharp electrode tip 1685 is not insulated. At a solder point 1684 disposed at its proximal end the electrode body 1683 is connected to a control unit 10 via a thin flexible copper wire 1686. The electrode 1683 is enclosed, except at the solder point 1684, by a first glucose/sodium hyaluronate matrix body 1690 (95:5, w/w) in which particulate nifedipine (0.05 mg per electrode, 5-10 µm (90%)) is evenly distributed. The first glucose/gelatin matrix 1690 is covered, in turn, by a second glucose/sodium hyaluronate matrix 1693 of same composition except for that it comprises, instead of nifedipine, 0.1 mg of human heparin. The second glucose/sodium hyaluronate matrix layer 1693 is coated with a thin layer 1692 of low-molecular weight carboxymethyl cellulose comprising 10-15 i.u. of hyaluronidase.

Figures 19, 19A:
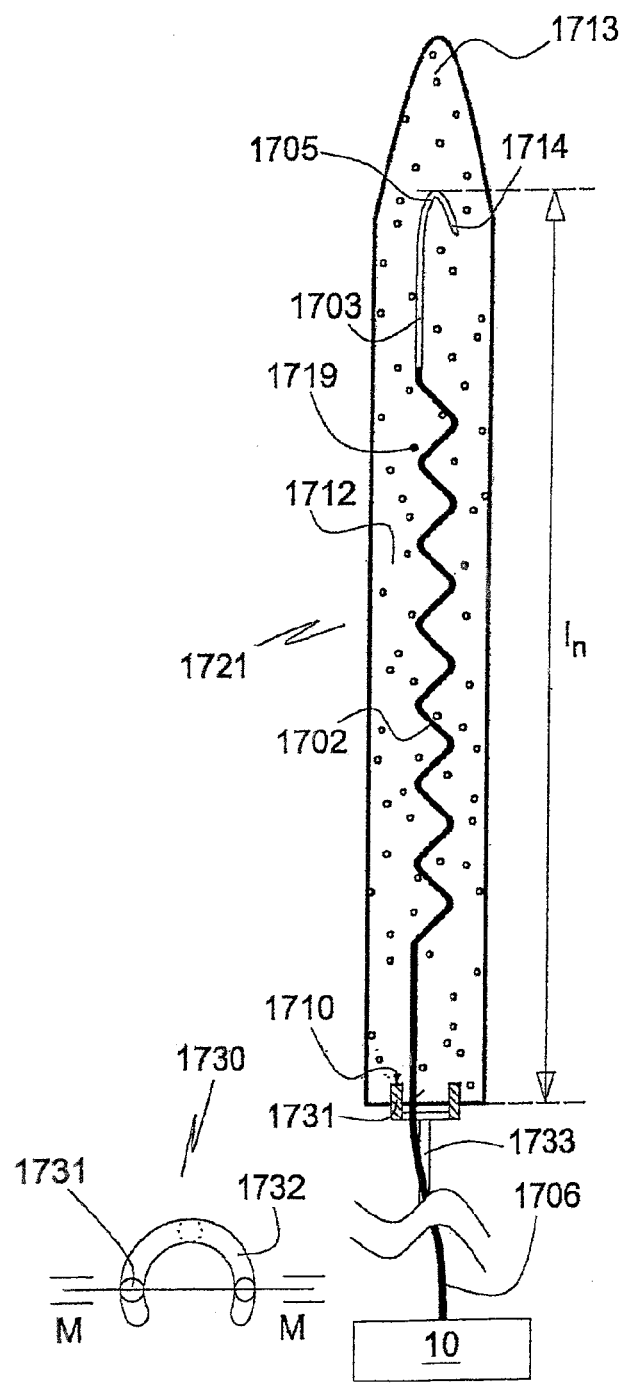
FIG. 19 illustrates an additional embodiment of the electrode of the invention in an axial section M-M (FIG. 19a) comprising an electrode body made from a single metal wire that also provides for electrical connection of the electrode body to a control unit. The electrode is shown mounted on a tissue insertion tool.
FIG. 19a is a top view of the tissue insertion tool of FIG. 19 in a proximal direction.

An additional embodiment 1721 of the electrode of the invention is shown in FIG. 19. The extendable electrode body of gold-plated silver consisting of a tip section 1703 ending in a hook 1714 and a main body section 1702 is embedded in a matrix body 1712 of glucose/low molecular weight polyvinylpyrrolidone 8:2 (w/w), in which starch microcapsules 1719 containing 10% by weight of sodium pyruvate are distributed. The electrode body 1702, 1703 is fully embedded in the matrix body 1712, and is integral with a flexible electric conductor 1706 of same material and diameter. The conductor 1706 and the electrode body 1702, 1703 is made from a single gold-plated silver wire insulated by a thin coat of polyamide (not shown), which is removed from the tip section 1703 after the electrode body has been given its zig-zag shape. Finally the tip section 1703 is been bent to form the hook 1714. The nominal length $l_n$ of the electrode body 1702, 1703 is defined by the length of the shaped wire embedded in the matrix body 1712. The matrix body 1712 has the form of a projectile with a flat rear (proximal) face and a blunt distal tip 1713. The rear face of the matrix body 1712 is provided with two bores 1710 for insertion of coupling pins 1731 extending from an about hemicircular support element 1732 of an electrode insertion tool 1730. From the opposite face of the support element 1732A extends in the opposite direction a manipulating rod 1733 for handing by the person performing insertion of the electrode into tissue. The electrode body 1702, 1703 is coupled to an electrode control unit 10 via the flexible conductor 1706.

Figure 20:
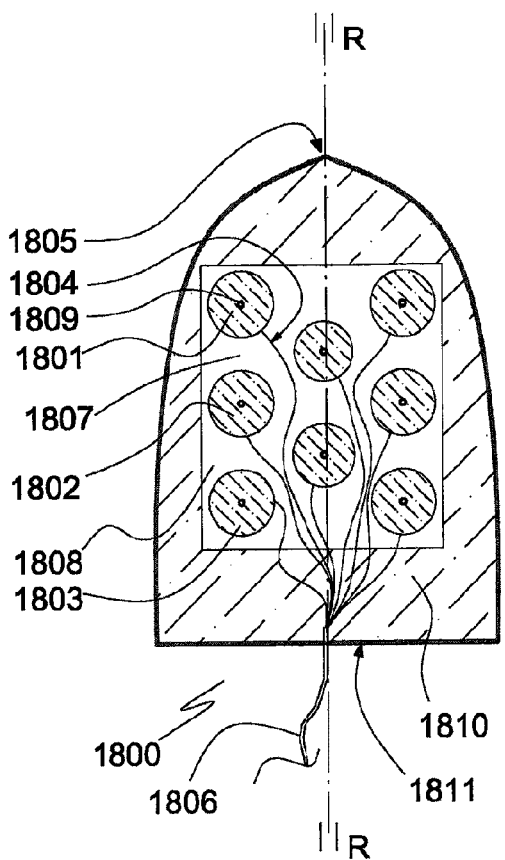
FIG. 20 is an about axial section through an electrode array of the invention at a level slightly above the base plate but with the base plate shown.

An embodiment of the array 1800 of electrodes of the invention is illustrated in FIG. 20. The array comprises a base plate 1808 of poly(lactide-co-glycolide) in which electrode bodies 1809 of the invention are secured at their second ends. Insulated thin gold wires 1804, which are electrically connected with their rear ends of the electrode bodies 1809, are assembled in a shielded lead 1806. The lead 1806 is electrically connected with a microprocessor control unit (not shown). A short rear end portion of the electrode bodies 1809 extends out of the respective electrode matrices 1801, 1802, 1803. All aforementioned elements are enclosed in a carbohydrate array matrix body 1810 of a matrix material designed to dissolve within a couple of minutes in contact with soft tissue. Of the entire array 1810 is only the lead 1806 that extends out of the matrix body. The matrix body 1804 is about bomb-shell shaped with a central axis R-R and has a blunt tip 1805 and a flat rear face 1811. Upon insertion of the array 1800 into soft tissue in an axial direction with the tip 1805 foremost the array matrix dissolves quickly. The electrodes with their matrices 1801, 1802, 1803 are now extending like hairs of a brush about perpendicularly from the base plate 1808. Except for the rear end portion of their electrode bodies extending out of the respective matrices the electrodes of the array 1800 correspond to the electrode of FIG. 17a. The adjacent tissue (not shown), which is now abutting the tips of the matrices 1801, 1802, 1803, is easily penetrated by them when displaced towards the tissue by the person carrying out the insertion of the array. This displacement is substantially in a direction perpendicular to the direction of insertion of the array in its original state. It can be carried out by manipulating the base plate 1808 by an array insertion instrument (not shown) that is releaseably coupled with the plate 1808 and allows to displace the plate 1808 in both directions, that is in directions perpendicular to each other. The matrices 1801, 1802, 1803 comprise a drug, which is released during their slow dissolution in the tissue. The dissolution process also establishes electric contact of the electrodes with the tissue and allows the registration of, for instance, nerve signals affected by the released drug. An array of electrode bundles (not shown) can be designed in a similar manner, the electrodes of FIG. 20 being substituted by electrode bundles, and can be manipulated correspondingly.

An array of electrode bundles (not shown) can be designed in a similar manner, the electrodes of FIG. 20 being substituted by electrode bundles, and can be manipulated correspondingly.

Manufacture of the Drug-Releasing Medical Electrode, Electrode Bundle and Electrode Bundle Array of the Invention Below, first the manufacture of individual components of the drug-releasing medical electrode, the electrode bundle and the electrode bundle array of the invention is described, then their assemblage to the drug-releasing medical electrode, the electrode bundle and the electrode bundle array of the invention.

Electrode Coating

The following general procedures describes the generation of a rapid to medium release coating on an electrode. A coating of an electrode (described above) can be accomplished by using a single technique or combinations of techniques exemplified by but not limited to dip coating, spray coating, melting processes including extrusion, compression molding and injection molding or a combination of different techniques.

In a illustrative example of a stepwise procedure, the electrode is first dip-coated with a suitable resorbable polymer or blend of polymers from the listed polymers above especially collagen, gelatine, polyvinyl alcohol and starch dissolved in a proper solvent.

Polymers can also be used. The thickness of the polymer layer is thoroughly controlled in ways known for those skilled in the art. The coating is then subjected to a drying step. The dip coating and drying steps could be done once or repeatedly depending on required thickness of the final coating. In the next step the drug is loaded into the polymer. The electrode is submerged into a solution containing the drug. The solvent should resorb the polymer as well as dissolving the drug. After an optimum time the electrode is removed from the solution and the matrix is dried. In a one pot procedure the electrode is submerged into a solution containing a suitable polymer and a drug of choose in a concentration optimum for a required matrix thickness and drug loading. The electrode is removed from the solution and then dried. The coating could also be generated by spray coating where the polymer/drug solution is sprayed on the electrode. The thickness of the coating may be controlled by the number of spraying and drying cycles and the amount of polymer and additive in the solution.

Electrodes for Temperature and Electrically Induced Release

The above mentioned methods are applicable for these applications using a proper polymer or polymer blend with optional additives and a drug of choose. Examples of polymers or polymer blends with optional additives are for temperature control: fully or intermediately hydrolyzed water-soluble resins such as polyvinyl alcohol. Polyacrylic acid or derivative thereof, e.g., poly(N-isopropylacrylamide) gel, and the increase in temperature causes the hydrogel to contract, thereby forcing the drug out of the coating. Alternatively, the temperature-sensitive hydrogel is an interpenetrating hydrogel network of poly(acrylamide) and poly (acrylic acid), and the increase in temperature causes the hydrogel to swell, thereby allowing the drug to diffuse out of the gel. (Dinarvand et al. 1995; WO 2005/067896; U.S. Pat. No. 7,066,904). Examples of polymers or polymer blends with optional additives are for electrically triggered release: polyvinyl alcohol/Chitosan (Seon Jeong Kim et al., 2002. J Appl Polymer Sci), polyvinyl alcohol/poly acrylic acid (Li L et al. 2005. Nanotechnology 16, 2852-2860), Microencapsulation of Drugs In one preferred embodiment of the invention the bioactive components are encapsulated in microspheres. Microspheres can range in size from few nanometers to millimetres in diameter. The following microencapsulation technologies can be used but not limited to in obtaining microspheres: spray drying, spray chilling, rotary disk atomization, fluid bed coating, stationary nozzle coextrusion, centrifugal head coextrusion, submerged nozzle coextrusion, pan coating, phase separation, solvent evaporation, solvent extraction, interfacial polymerization, coacervation, in-situ polymerization, liposome technology, nanoencapsulation. Standard methods for the manufacture of microspheres are given in: Microencapsulation: Methods and Industrial Applications. S Benita 1996 ISBN-10: 0824797035, which is incorporated herein by reference.

The following shell-building materials are particularly useful for producing microcapsules: proteins, polysaccharides, starches, waxes, fats, other natural and synthetic polymers. Optionally, the one or more additives to the shell building materials can be used to increase or decrease the drug release rate from the microcapsules. An optimal release rate of the encapsulated drug can be achieved by the selection of the shell material, the size of the spheres, type and amount of embedded drug and additives incorporated in the spheres. The drug release rate of microspheres is commonly of first order. However, microcapsules exhibiting zero order release rates are also known in the art. A microsphere of the invention may contain smaller spheres in which the drug is embedded. Spheres can be designed to be dissolvable using the materials listed for the matrix above but with a slower dissolvability than the surrounding matrix. Alternatively the spheres can be designed to be non-dissolvable using more biostable materials. For example, biocompatible synthetic polymers such as polyurethane (including polycarbonate urethanes), isobutylene, polystyrene-isobutylene-polystyrene, silicone (e.g., polysiloxane and substituted polysiloxane), a thermoplastic elastomer, ethylene vinyl acetate copolymer, a polyolefin elastomer, EPDM ethylene-propylene terpolymer rubber, polyamide elastomer, hydrogel or combinations thereof (WO 2005/082430). Such hydrogel polymers include, but are not limited to, derivatives of 2-hydroxyethylmethacrylate, polyvinyl alcohol, polyethylene oxide, polyethylene glycol, polyurethane hydrogel, naturally occurring hydrogels, e.g., gelatin, hyaluronic acid, cross-linked albumin, etc. or combinations thereof. (WO 2005/082430).

For instance, when microencapsulation is conducted by an in-water drying method, said w/o emulsion is further added to another aqueous phase (hereafter referred to as an external aqueous phase) to yield a w/o/w emulsion, followed by removing an organic solvent in an oil phase, to yield microcapsules. An emulsifier may be added to the above-described external aqueous phase. Any pharmaceutically acceptable emulsifier can be used, as long as it generally produces a stable w/o/w emulsion. Examples of such emulsifiers include anionic surfactants (e.g., sodium oleate, sodium stearate, sodium lauryl sulfate), nonionic surfactants (e.g., Tween 80, Tween 60, HCO-60, HCO-70), polyvinyl alcohol, polyvinylpyrrolidone and gelatin. Two or more of these emulsifiers may be used in combination in an appropriate ratio. The emulsifier concentration in an external aqueous phase ranges for instance from about 0.01 to about 20%, preferably from about 0.05 to about 10%.

Removal of an organic solvent from microcapsules can be achieved by known methods, including the method in which the solvent is removed under normal or gradually reduced pressure during stirring using a propeller stirrer, magnetic stirrer or the like, and the method in which the solvent is removed while the degree of vacuum and temperature are adjusted using a rotary evaporator or the like.

The thus-obtained microcapsules are centrifuged or filtered to separate them, and subsequently washed with distilled water several times repeatedly to remove the free physiologically active substance, drug-retaining substance, emulsifier etc. adhering to the microcapsule surface. Then, washed microcapsules are dried under reduced pressure or freeze-dried after re-dispersion in distilled water to further remove an organic solvent.

For producing microspheres by a phase separation method, a coacervating agent is gradually added to a w/o emulsion while the emulsion is stirred, to precipitate and solidify a polymer of lactic acid. Any pharmaceutically acceptable coacervation agent can be used, in particular a mineral or vegetable oil miscible with the polymer solvent and which does not dissolve the polymer used for encapsulation. Examples of such coacervation agents include silicone oil, sesame oil, soybean oil, corn oil, cotton seed oil, coconut oil, linseed oil, mineral oil, n-hexane and n-heptane. Two or more of these may be used in combination. The amount of the coacervation agent used is, for instance, about 0.01 to about 1,000 times by volume, preferably about 0.1 to about 200 times by volume, relative to a w/o emulsion. The thus-obtained microspheres are centrifuged or filtered to separate them, after which they are repeatedly washed with a wash such as hexane and heptane to remove the coacervating agent. Then the wash is evaporated by heating or decompression.

If necessary, in the same manner as with the above-described in-water drying method, a free physiologically active substance and an organic solvent are removed.

For producing microcapsules by a spray drying method, a w/o emulsion or a w/o/w emulsion produced in the same manner as in an in-water drying method is sprayed by a nozzle into the drying chamber of a spray drier to volatilize an organic solvent and water in the fine droplets in a very short time so as to yield microcapsules. Examples of the nozzle include, for instance, a two-fluid nozzle type, a pressure nozzle type and a rotary disc type. If necessary, microcapsules thus obtained are washed with distilled water several times repeatedly to remove a free physiologically active substance, a drug-retaining substance, an emulsifier, etc. adhering to the microcapsule surface. Then, washed microcapsules may be dried under reduced pressure or freeze-dried after redispersion in distilled water to further remove an organic solvent.

Also, when a physiologically active substance dissolves 1) in an oil phase consisting of one hydrophobic organic solvent (e.g., dichloromethane, chloroform, dichloroethane, carbon tetrachloride, ethyl acetate, cyclohexane) and at least one hydrophobic organic solvent (e.g., methanol, ethanol, acetonitrile), or 2) in an oil phase consisting of a polymer solution in a hydrophobic organic solvent, or 3) in an oil phase prepared by adding at least one surfactant (e.g., glycerol fatty acid ester, propylene glycol fatty acid ester, sucrose fatty acid ester) to the above-described hydrophobic organic solvent; these oil phases may be dispersed in an external aqueous phase used in the above-described in-water drying method to yield an o/w emulsion, followed by removing an organic solvent in the oil phase in the same manner as in the above-described in-water drying method, to yield microcapsules. Further, this o/w emulsion can be subjected to the above-described phase separation method or spray drying method to prepare microcapsules.

The sustained-release preparation of the present invention preferably comprises an excipient. The excipient is desired to be low in toxicity when administered to a living body; be easy to dry by freeze-drying or spray-drying; and dissolve rapidly when administered to a living body or dissolve at the time of use. Examples of such excipient includes, for instance, sugars, cellulose derivatives, amino acids, proteins, polyacrylic acid derivatives, organic salts and inorganic salts. Two or more of these excipients may be used in combination in an appropriate ratio.

Dissolvable or Degradable Bars Containing Drugs

Bars or rods of drug-conjugation material may be fabricated by dispensing a drug on a sheet-formed material dissolvable in a body fluid and then cover the drug with a material of same kind. Alternatively, a drug may be applied on a surface of a coating material followed by covering the drug layer with the same kind of coating material. The S-layer sheet is then cut into thin straps. One or more straps are disposed parallel with an electrode of the invention prior to enclosing the electrode and the straps with matrix material. Similarly, stiff rods of a material dissolvable in a body fluid or a biodegradable material comprising a drug can be formed separately and enclosed in a matrix material in combination with and adjacent to an electrode of the invention. Suitable rod materials are for example, synthetic biocompatible polymers such as, for example, polyurethane (including polycarbonate urethanes), isobutylene, polystyrene-isobutylene-polystyrene, silicone (e.g., polysiloxane and substituted polysiloxane), a thermoplastic elastomer, an ethylene vinyl acetate copolymer, a polyolefin elastomer, EPDM ethylene-propylene terpolymer rubber, polyamide elastomer, hydrogel or combinations thereof (WO 2005082430). Such hydrogel polymers include, but are not limited to, derivatives of 2-hydroxyethylmethacrylate, polyvinyl alcohol, polyethylene oxide, polyethylene glycol, polyurethane hydrogel, naturally occurring hydrogels, e.g., gelatin, hyaluronic acid, cross-linked albumin, etc. or combinations thereof. (WO 2005082430). Alternatively an electrode that is only partially insulated such as being covered by an insulating material only proximally or that consists of multiple sites that are not insulated can be used to control the release of drugs.

The bars or rods are preferably introduced into the middle of the electrode bundle. Other locations within the electrode are also possible. The bars may be attached to individual electrodes to follow their course during the unfolding process. In this case, the bars need to be relatively flexible and should have a diameter similar to that of the individual electrode, although other dimensions are also possible. Bars may also be relatively stiff in cases where it is desirable to let the bars follow the main track line during insertion and drugs will then only be released from the cord of each electrode or electrode bundle. The bars may in this case serve a dual role of releasing drugs and adding to the stiffness of the entire electrode ensemble during implantation.

Embedding Electrodes and Drugs in a Matrix

Drugs can be incorporated into a matrix or a matrix compartment by blending the drugs with the materials used to build the matrix or matrix sub-compartment, and/or by blending microspheres with the matrix materials or matrix compartment material. Also, ready-made bars or rods of a biodegradable material or material dissolvable in a body fluid containing a drug can be inserted in parallel with the electrodes. The electrodes can be coated with one or more layers of drug containing matrix material and/or drug containing matrix sub-compartment material. By choice of different materials for matrix compartments different drug release rates can be obtained. The combination of different matrix or matrix sub-compartment layers, drug-containing microspheres and bars should be stable, i.e. outer layers should not in any aspect affect the inner layers/structures prior to implantation. The electrode or electrode bundle or electrode bundle array of the invention is disposed in a sheath of a smooth material of low wettability such as a polyfluorinated hydrocarbon polymer or silicon rubber, and fixed therein. The sheath thus functions as a mould. To facilitate solvent evaporation the sheath material is advantageously porous, in particular micro-porous. After adding the matrix or matrix compartment material comprising the drug, optionally a microencapsulated form into the sheath and drying (evaporating the solvent, optionally under reduced pressure), the product is withdrawn from the sheath.

The sheath can have the same form as the final probe but may also be of smaller size in case more material is subsequently added to the probe by dip coating or spray coating. To facilitate handling of the electrodes or other components such as bars containing drugs, optical fibers or bimetal, a micromanipulator attached to the components by a dissolvable glue is used to insert them into the mould. Moreover, the individual electrodes may preferably be arranged in specified pattern and then spray coated or dip coated to become fixated to each other before being submerged into the matrix. The material used to fixate the electrodes or other components in a certain configuration is preferably made of the same dissolvable materials as that constituting the matrix. The method comprises the manufacture of a matrix material containing drugs of choice and/or microspheres. This can be accomplished by simply dissolving the drugs or microspheres in the material used to produce a certain matrix compartment.

In addition, the method comprises providing a fixation means, fixing the electrodes and bars containing drugs, and optionally additional elements to be imbedded, such as optical fibres, contractile elements, etc., in the fixation means in a desired configuration as described above, applying a sheath covering the thus fixed elements except for at the proximal coupling section thereof, applying a solution or suspension of a first matrix material on the electrode in a manner so as to cover the portions of the elements intended to be embedded, allowing the solvent/dispersant of the matrix solution or suspension, respectively, to evaporate or harden, removing the sheath, and releasing the elements from the fixation means. For embedment of the electrodes and other elements in two matrix materials so as to form corresponding matrix compartments, each enclosing a portion of the electrode, an appropriate portion of the electrode fixed by a fixation means as described above is coated with a solution or suspension of the first matrix material, the solvent/dispersant of which is subsequently evaporated, followed by coating the portion of the electrode remaining to be coated with a solution or suspension of the second matrix material, subsequently evaporating the solvent/dispersant of the second matrix material, and releasing the electrode from the fixation means.

An alternative method of embedding an electrode of the invention into two matrix materials forming distinct matrix compartments into which portions of the electrode are embedded, comprises embedding the entire electrode in a first matrix material, dissolving a portion of the first matrix material, preferably a distal portion extending from the distal end, covering the now non-embedded distal portion of the electrode with a second matrix material by, for instance, taking recourse to a sheath applied on the non-embedded distal portion, filling the sheath with a solution or suspension of the second matrix material, evaporating the solvent so as to dry/harden the second matrix material, and removing the sheath.

Defined compartments within the matrix containing releasable bioactive molecules can be achieved so as to focus the drug effects to the tip regions or to the shank region of the electrodes. This can be achieved by manufacturing the matrix—electrode construction in two or more steps, each step adding on a compartment.

Materials and Dimensions

Electrode dimensions. The electrodes of the invention have a suitable diameter of from $10^{-4}$ to $10^{-7}$ m, in particular of from 0.5 to 25 µm. A larger wire diameter, such as, up to $1.5 \times 10^{-3}$ m may be used in case a gross stimulation/recording paradigm is used, for example to produce lesions in soft tissue. Their diameter may change over their length to facilitate insertion into the tissue, in particular the electrode can be tapering towards their distal end. Their distal end can be sharp or blunt but a sharp tip is preferred in case of the electrode being used for recording of electrical activity. Their distal part may even have a diameter smaller than $10^{-7}$ m.

The surface of electrodes may be smooth or not or partially smooth and partially not smooth, that is, rough. An uneven or rugged surface close to the electrode tip is preferred for improving the anchoring properties and for reducing the impedance of the electrode tip. The electrode of the invention is preferably insulated except for at portions extending from their proximal and distal ends. However, the electrode body may also be equipped with means to allow stimulation/recordings at multiples sites within the tissue. Such means may, for example, consist of electrically conductive protruding ultra-thin filaments, or portions with a rough or uneven surface occupying a length of up to 10 µm or more. Such regions are not electrically insulated if an electrical contact with the tissue is intended. They may also serve as anchoring means and, in addition, as for electrical stimulation/recording. If electrical stimulation of a larger volume of tissue is intended, it is alternatively preferred not to insulate a larger portion extending from the electrode tip, such as a length of up to 100 µm or even up to 1 mm. Suitable for insulation of the electrode wires are, for instance, glass, polyvinyl formal, parylene C, polyxylene, epoxy resin, polyamide, silicon rubber, water-insoluble lacquer.

Electrode shape. An important feature of the present invention is that the distance from the distal tip to the proximal coupling section of the electrode can be repetitively and reversibly increased and decreased without rupture of the electrode so as to permit the wire to smoothly follow non-uniform movements in surrounding soft tissue, such as may occur in the vicinity of arterial or venous vessels, the heart or the lungs or between soft and hard tissue. This is achieved by equipping the electrode with multiple bends, which may follow a given pattern or not. The electrodes thus can have a wavy, curly, tortuous, spiral or otherwise not straight configuration, which allows the distance from the proximal coupling section to the distal tip section to be easily increased/decreased by at least 1%, but preferably by at least 5% when force is exerted along the wire. For example, the distance from tip to base of an electrode of 1 mm in length can be easily increased/decreased by at least 10 µm, and even by 50 µm or more.

It is preferred to use a smooth bending pattern, such as a wavy or spiral pattern. A pattern characterized by abrupt bends is less preferred, since the forces caused by increasing/decreasing the distance between the tip and the proximal coupling section of the electrode should not substantially affect particular sites on or short sections along the electrode body, but should rather affect larger sections. This will increase the endurance of an electrode exposed to continuous changes in length by the movement of surrounding living tissue. Although not preferred, it is within the ambit of the invention to use elastic conductive wires coated with an elastic insulation material, such as silicone rubber. Moreover, other types of electrodes, such as straight electrode wires or electrodes mounted on flexible chips, may be used in tissue regions that do not exhibit substantial movement along the electrode axis.

Electrode materials. To approach the ratio of electrode density to tissue density, and thereby reduce the difference in inertia between the electrode and the tissue, the electrode of the invention comprises a core of a light and strong non-conductive material such as natural protein fibre, for instance silk, or polymer fibre covered by an electrically conductive material. Alternatively a tubiform supportive material filled with an electrically conductive material such as a metal, in particular a noble metal or a noble metal alloy, but also carbon may be used; in this case the supportive material may additionally act as an electrical insulator. Other examples of useful non-conductive core or tubiform supporting materials are glass and ceramic. The electrically conductive material can be deposited on the support material by conventional sputtering or evaporation techniques. Optionally, the electrode of the invention can comprise an electrically conductive metal core of, in particular, gold, platinum, titanium, stainless steel, an alloy comprising more than 30% by weight of noble metal such as iridium, the combination of platinum and iridium, and tungsten, but also of an electrically conductive polymer.

Exemplary Uses

Preferred uses of the electrode of the invention as well as bundles of the electrode of the invention and arrays of the electrode of the invention and/or of bundles of the electrode of the invention are described in the following.

Clinical use. For aiding patients after brain/spinal damage by recording signals from remaining neurons in case of, for instance, stroke or degenerative disease and/or stimulating neurons to compensate for lost functions. Similar uses are possible in animals. In particular: pain relief by stimulation of analgesic brain stem centres, such as nuclei in the periaqueductal grey substance; relief or decrease of tremor in Parkinson's disease, choreatic and other involuntary movements by stimulation within the basal ganglia or associated nuclei; boosting memory by stimulation of cholinergic and/or monoaminergic nuclei in case of Alzheimer's disease or other degenerative diseases; control of mood, aggression, anxiety, phobia, affect, sexual over-activity, impotence, eating disturbances by stimulation of limbic centers or other brain areas; rehabilitation of patients after stroke or damage of the brain/spinal cord by stimulation of remaining connections in the cortex cerebri or descending motor pathways; re-establishment of control of spinal functions such as bladder and bowel emptying after spinal cord injury by stimulating relevant parts in the spinal cord; control of spasticity by stimulation of inhibitory supraspinal descending centres or appropriate cerebellar areas; re-establishment of somatosensory, auditory, visual, olfactory senses by stimulation of relevant nuclei in the spinal cord and the brain. Other medical uses are also within the ambit of the invention.

Examples where recording is combined with stimulation include but are not limited to: monitoring of epileptic attacks by electrodes implanted into the epileptic focus—coupled to a system that deliver antiepileptic drugs or electrical pulses; compensating for lost connections in the motor system by recording central motor command and stimulating the executive parts of the motor system distal to the lesions; recordings of blood glucose levels to control the release of hormones. Implanted electrodes of the invention may also be used for local lesioning of tissue by passing current of sufficient magnitude through the electrodes. The multichannel design offers a possibility to selectively lesion particular areas in the tissue. This can be useful if a tumour or an abnormally active or epileptogenic nervous tissue has to be lesioned. In such cases, the electrodes may first be used to record and locate the disease followed by stimulation. The invention also permits combined local drug administration and stimulation as a therapy for treating cancer. Lesioning of tissue by passing current through the electrodes may also be combined with drug delivery, for example of growth factors prior to implantation of new tissue to create a favourable situation for the new implant.

It is also possible to combine stimulation and recording with release of embedded analgesics or antiepileptic drugs, embedded drugs such as neurotrophic substances, antioxidants or drugs antagonizing apoptosis to halt or alleviate disease processes. Combined stimulation and release of trophic factors can also be used to trigger regenerative processes and learning mechanisms (similar to what is seen during development) with the aim of guiding functional recovery.

Use in research and drug development. To study the normal and pathological functions of the brain and spinal cord, it is necessary to be able to record neuronal activity and, at the same time, interact with the undisturbed central nervous system (CNS). For this purpose, the electrodes, electrode bundles and arrays of electrode bundles of the invention will have to be implanted in CNS for a long time. Due to their design and dimensions they can be left securely in the CNS for a very long time. The invention permits continuous measurements of the neuronal in any of the different brain centers to gauge the function, activation pattern, and abnormal activity in the center. These measurements can then be used to test the effects of various bioactive molecules administrated systemically or locally. Bioactive molecules include substances acting, for example, through receptor activation but also vector systems mediating gene transfer. By inducing the expression of specific genes in cells in the neighbourhood of the electrode(s) effect equivalent to pharmacological treatment can be achieved of extended periods of time, such as days and even weeks, and many fundamental cell properties can be permanently altered for experimental or therapeutic purposes.

For example, the electrodes may be used to monitor pain related signals for a long time in nociceptive pathways to the cortex cerebri in animal models of pain. Moreover, due to its embedded drugs it is possible to reduce the complications that may occur during and after implantation such as bleedings, infections, inflammation, apoptosis etc, and which, if left unattended, would have complicated the interpretation of the results from the electrodes.

The electrodes of the invention may also be used to record and stimulate nerve fibers or their somata in the peripheral nervous system (PNS).

Combinations of electrical stimulation/recordings and drug delivery are also possible. Due to that the embedded means for local drug delivery are configurationally locked to the electrodes during implantation, it is possible to embed a variety of bioactive molecules and measure their local and distant effects on the tissue.

A particularly useful application is to use the invention to measure the effects on the central nervous system and peripheral nervous system of many different types of bioactive molecules simultaneously. This can be achieved if the coating of different electrodes of the invention contains different bioactive molecules/drugs since these drugs will be released close to the respective electrodes. Using bundles of electrodes or arrays of electrodes/bundles of electrodes where individual recording electrodes are coated with different bioactive molecules opens up possibilities for high performance screening of the effects of multiple potentials therapeutic drugs. Such a screening of potential drugs may also be used in combination with electrical stimulation or stimulation produced release of bioactive molecules. For example, it is possible to simultaneously record the effects of different bioactive molecules on pathological activity caused by either active or passive local release of neurotoxins from embedded drug compartments.

Combined recording and release of key molecules can be used to study physiological effects of molecular manipulations in intact functional circuits—such as manipulations of signalling pathways in plasticity pathways underlying learning in natural situations.

Voltametric measurements of concentrations of specific physiologically or pharmacologically relevant molecules (time resolution in ms). This will make it possible to follow the local effect of e.g. a drug on concentrations of specific molecules in real time in intact behaving animals. Combined measurements of the release of transmitter substance (such as dopamine, serotonin, noradrenalin, acetylcholine, neuropeptides etc) and recordings/stimulations can be used to study disease processes. Measurements of release may also be used to construct feedback systems. For example, by measuring the release of dopamine it is possible to construct a system that stimulate the dopaminergic neurons when they under-perform.

The invention can be used to combat bleedings during surgery or after stroke—by a combination of electrical stimulation that coagulates the tissue and local release of drugs producing vasoconstrictions and promoting coagulations during bleedings.

Use as an Interface for Interaction with Computers and Neuroprosthetic Devices. In patients with damage to the peripheral nervous system, it can be useful to record command signals from CNS. These signals can then be interpreted by computer programs and used to guide activity in neuroprostheses, such as artificial hands or feet, guide stimulation of muscles and organs such as the bladder and bowel. Implanted electrodes of the invention may also be used to monitor the health status of for example patients undergoing surgery, disabled or senile patients and be connected with health surveillance systems to improve patient care.

The electrodes of the invention can, either through wire-connections or telemetric equipment, communicate with measurement equipment of various kind, such as amplifiers, stimulators and computers.

Use in controlling the function of endocrine and exocrine organs. In patients with a deficient hormone secretion or regulation, the electrode, electrode bundle or array of electrodes and/or electrode bundles of the invention may be used to control the secretion of hormones from exocrine or endocrine organs or brain structures controlling such organs, for example the hypothalamus and certain brain stem nuclei. Combinations of drug delivery and electrical stimulation/recordings may be useful in scientific studies of neuronal systems and in studies of tissue reactions.

What is claimed is:

1. A medical microelectrode for insertion into soft tissue, the medical microelectrode comprising:
   an electrically conducting elongate electrode body including a first proximal end, and a second distal end, the electrode body comprising:
   a tip section extending from the distal end;
   a main body section extending in a proximal direction from the tip section,
   wherein the tip section, and the main body element are embedded in a first electrode matrix element, which is substantially rigid, biocompatible and soluble or biodegradable in a body fluid; and
   a second electrode matrix element, different from the first electrode matrix element, the second electrode matrix element positioned such that the first electrode matrix element is positioned between the second electrode matrix element and the electrode main body,
   wherein at least one of the first electrode matrix element and the second electrode matrix element comprises a drug configured to be released upon dissolution or biodegradation of the first electrode matrix element,
   wherein the electrode body comprises a non-conducting core, at least one electrically conducting layer on the core, and an insulating layer on the one or more electrically conducting layers,
   wherein the first electrode matrix element comprises a first drug, and the second electrode matrix element comprises a second drug different from the first drug.

2. The microelectrode of claim 1, wherein the tip section, and the main body section are fully embedded in the first electrode matrix element.

3. microelectrode of claim 1, wherein the diameter of the electrode body is from about $10^{-7}$ m to about $10^{-4}$ m.

4. The microelectrode of claim 3, wherein the coupling section is not embedded in the first electrode matrix element.

5. The microelectrode of claim 1, further comprising a coupling section extending in a proximal direction from the main body section.

6. The microelectrode of claim 1, further comprising a coating positioned to surround the second electrode matrix element.

7. The microelectrode of claim 1, wherein the first electrode matrix element comprises nifedipine, and the second electrode matrix element comprises heparin.

8. The microelectrode of claim 1, wherein the first electrode matrix element comprises glucose and gelatin and the second electrode matrix element comprises glucose and sodium hyaluronate.

* * * * *